(12) United States Patent
Orlow et al.

(10) Patent No.: US 7,378,232 B2
(45) Date of Patent: May 27, 2008

(54) ASSAY FOR MELANOGENESIS

(75) Inventors: Seth J. Orlow, New York, NY (US);
Prashiela Manga, Cincinnati, OH (US);
Liliana Staleva, New York, NY (US)

(73) Assignee: New York University, New York, NY (US)

( * ) Notice: Subject to any disclaimer, the term of this patent is extended or adjusted under 35 U.S.C. 154(b) by 352 days.

(21) Appl. No.: 10/435,439

(22) Filed: May 9, 2003

(65) Prior Publication Data

US 2004/0038328 A1    Feb. 26, 2004

Related U.S. Application Data

(60) Provisional application No. 60/412,536, filed on Sep. 20, 2002, provisional application No. 60/379,209, filed on May 9, 2002, now abandoned.

(51) Int. Cl.
*C12Q 1/00* (2006.01)
*C12Q 1/02* (2006.01)

(52) U.S. Cl. ............................................. 435/4; 435/29

(58) Field of Classification Search ...................... None
See application file for complete search history.

(56) References Cited

U.S. PATENT DOCUMENTS

| | | | |
|---|---|---|---|
| 5,066,489 A | 11/1991 | Paradise et al. | |
| 5,214,028 A | 5/1993 | Tomita et al. | |
| 5,389,611 A | 2/1995 | Tomita et al. | |
| 5,627,033 A | 5/1997 | Smith et al. | |
| 5,731,325 A | 3/1998 | Andrulis, Jr. et al. | |
| 5,789,215 A | 8/1998 | Berns et al. | |
| 5,814,618 A | 9/1998 | Bujard et al. | |
| 5,851,984 A | 12/1998 | Matthews et al. | |
| 6,132,740 A | 10/2000 | Hu | |
| 6,139,854 A | 10/2000 | Kawato | |
| 6,291,196 B1 | 9/2001 | Vielkind et al. | |
| 6,794,137 B2 | 9/2004 | Blumenberg | |
| 6,861,239 B1 | 3/2005 | Blumenberg et al. | |
| 6,953,664 B2 | 10/2005 | Blumenberg et al. | |
| 7,105,292 B2 | 9/2006 | Blumenberg | |
| 2002/0034772 A1 | 3/2002 | Orlow et al. | ............... 435/7.21 |
| 2004/0175767 A1 | 9/2004 | Orlow et al. | |
| 2006/0188953 A1 | 8/2006 | Orlow et al. | |

FOREIGN PATENT DOCUMENTS

| | | |
|---|---|---|
| WO | WO-88/09810 | 12/1988 |
| WO | WO 01/01131 A1 | 1/2001 |
| WO | WO-01/01131 A1 | 4/2001 |

OTHER PUBLICATIONS

Dooley et al. Development of an In Vitro Primary Screen for Skin Depigmentation and Antimelanoma Agents; Skin Pharmacol., vol. 7, Issue 4(1994) pp. 188-200.*

Goering et al. The Enigma of Arsenic Carcinogenesis: Role of Metabolism; Toxicological Sciences, vol. 49 (1999) pp. 5-14.*

Puri et al. Aberrant pH of Melanosomes in Pink-Eyed Dilution (P) Mutant Melanocytes; The Journal of Investigative Dermatology, vol. 115, No. 4 (2000) pp. 607-613.*

Manga, P. et al., Inverse Correlation Between Pink Eyed Dilution Protein Expression and Induction of Melanogenesis by Bafilomycin A1. Pigment Cell Research, 2001, vol. 14, No. 5, pp. 362-367.

U.S. Appl. No. 09/827,428, filed Mar. 21, 2002, Orlow et al.

Brilliant, M H. "The Mouse P (Pink-eyed Dilution) and Human P Genes, Oculocutaneous Albinism Type 2 (OCA2), and Melanosomal PH." *Pigment Cell Research.* Copenhagen, DK 143(2):86-93 (2001).

Chaudhuri et al., "apd1+, a Gene Required for Red Pigment Formation in *ade6* Mutants of *Schizosaccharomyces prmbe*, Encodes an Enzyme Required for Glutathione Biosynthesis: A Role for Glutathione and a Glutathione-Conjugate Pump", *Genetics* 145:75-83 (1997).

Del Marmol, Veronique et al. "Glutathione Depletion Increases Tyrosinase Activity in Human Melanoma Cells." *Journal of Investigative Dermatology*, 101(6):871-874 (1993).

European Search Report for European Patent Application No. 03 731 127.1 ,ailed Jul. 13, 2007.

Gahl et al., "Melanosomal Tyrosine Transport in Normal and Pink-eyed Dilution Murine Melanocyte", *Pigment. Cell. Res*, 8:229-233 (1995).

Gautier et al., "α-DNA IV; α-anomeric and β-anomeric tetrathymidylates Covalently Linked to Intercalcating Oxazolopyridocarbazole. Synthesis, physiochemical properties and poly (rA) binding", *Nucl. Acids Res.*, 15:6625-6641 (1987).

Gilchrest et al., "The Pathogenesis of Melanoma Induced by Ultravioled Radiation", *New England J. Med.*, 340:1341-1348 (1999).

Helmbach et al., "Drug-Resistance in Human Melanom", *In"nt. J. Cancer*, 93:617-622 (2001).

van der Krol et al., "Modulation of Eukaryotic Gene Expression by Complementary RNA or DNA Sequences", *BioTechniques* 6:958-976 (1988).

Kromberg et al., "Albinism and Skin Cancer in Southern Africa",*Clin. Genet.*, 36:43-52 (1989).

Lee, S-T et al. "Organization and Sequence of the Human P Gene and Identification of New Family of Transport Proteins", *Genomics.* Academic Press, San Diego, 26(2):354-363 (1995).

(Continued)

*Primary Examiner*—Jon Weber
*Assistant Examiner*—Paul Martin
(74) *Attorney, Agent, or Firm*—Wilmer Cutler Pickering Hale & Dorr LLP

(57) ABSTRACT

The invention provides methods for the identification of agents that modify or mimic P protein function. Cells expressing a P protein are generally more sensitive to toxins, and changes in cell viability and/or cell death after exposure of P protein-expressing cells to an agent and a toxin is an indication that such an agent is a modifier of P protein expression. The invention also provides methods for the treatment of melanoma and other cancers.

28 Claims, 11 Drawing Sheets

OTHER PUBLICATIONS

Figure 1A:
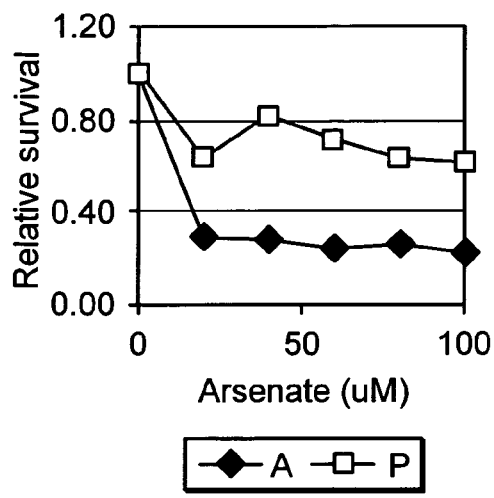
Figure 1B:
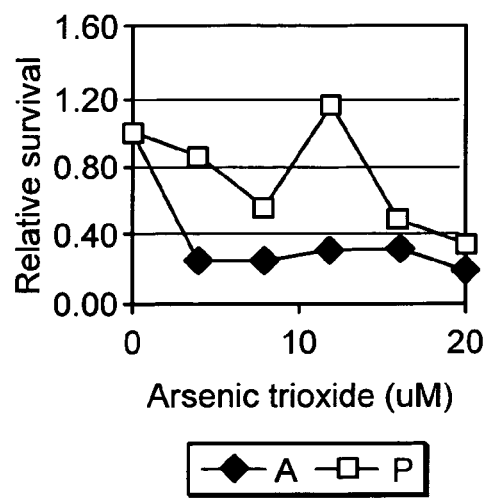
Figure 1C:
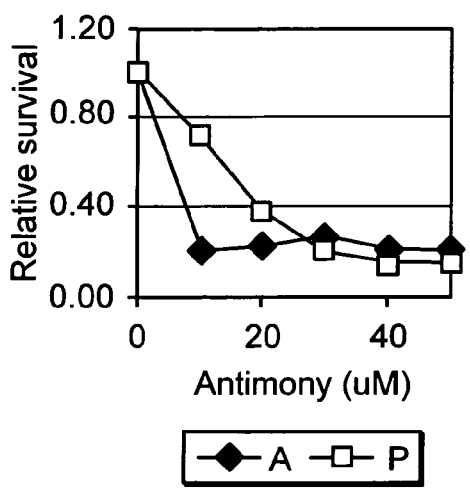
Figure 1D:
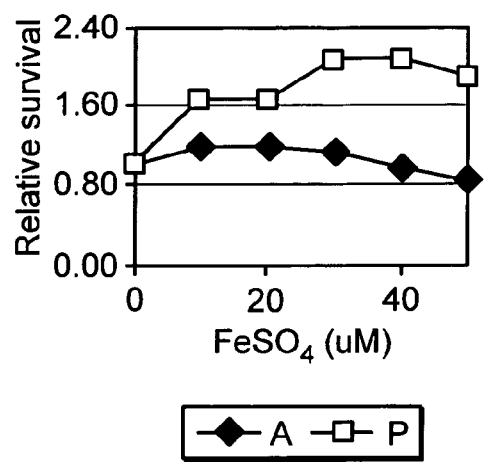
Figure 1E:
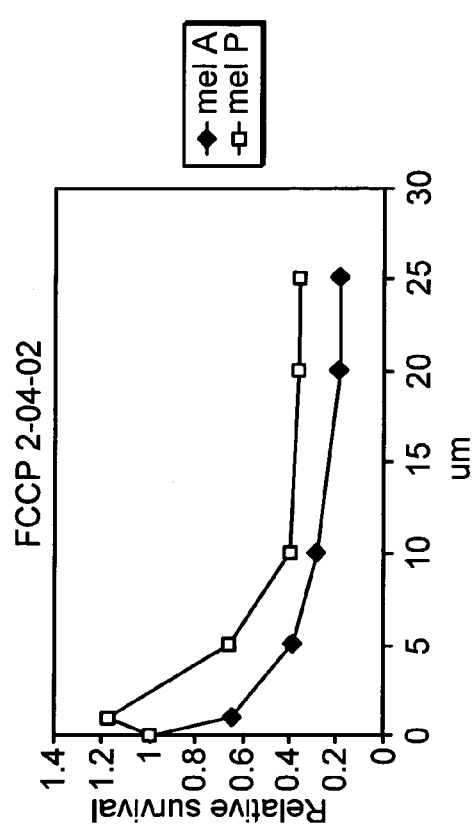
Figure 1F:
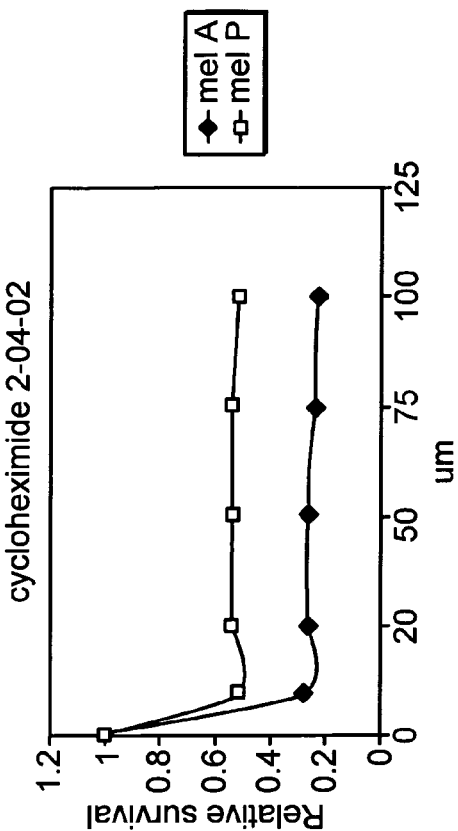
Figure 1G:
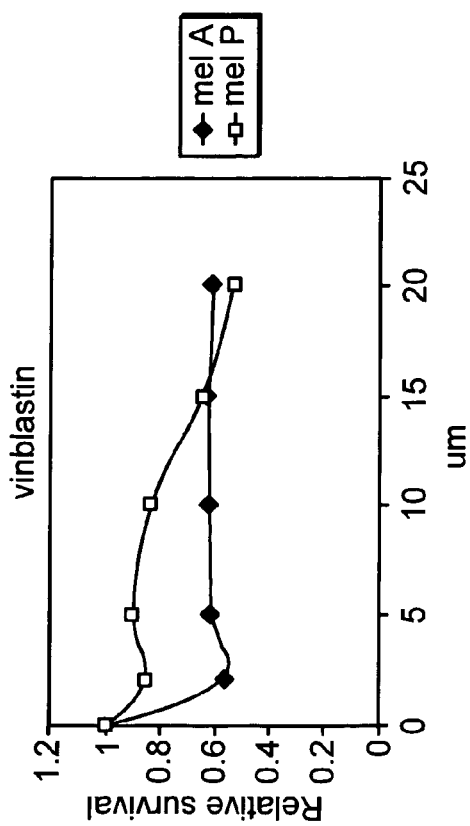
Figure 1H:
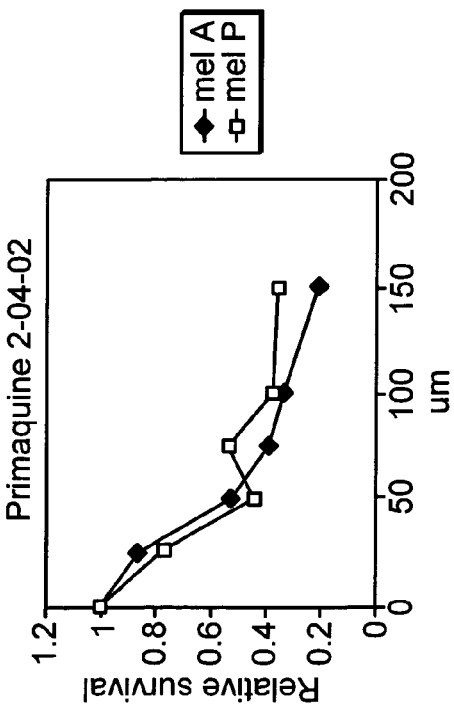
Figure 1L:
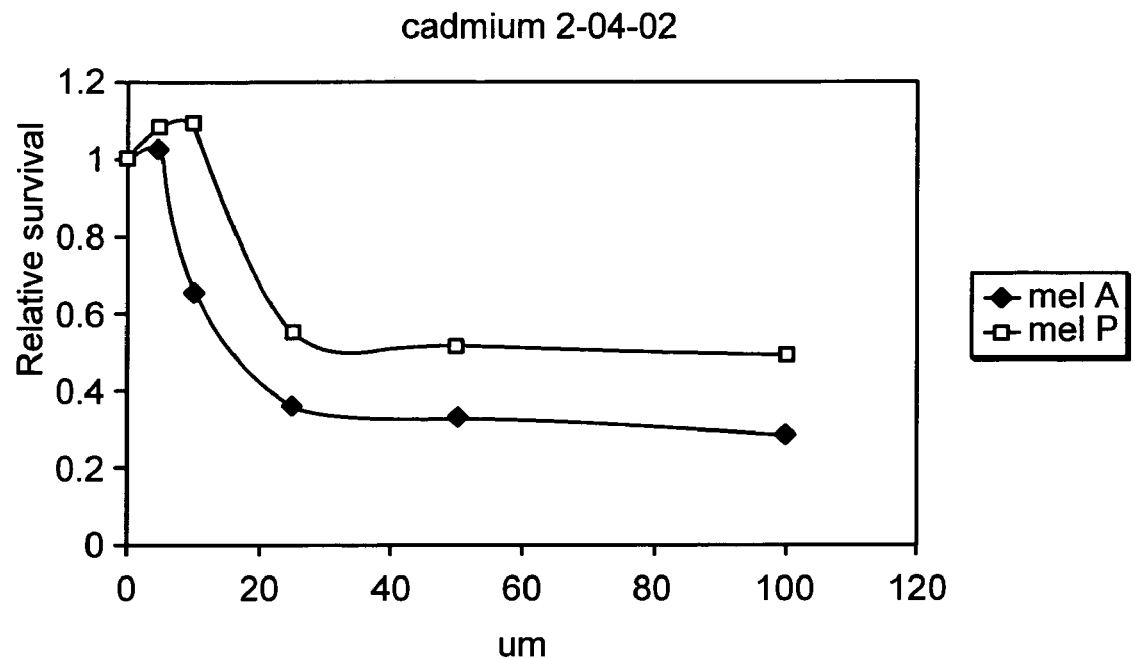
Figure 1M:
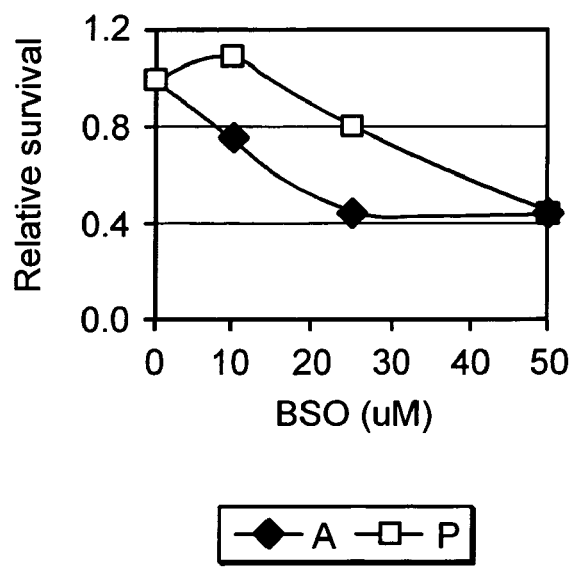
Figure 1N:
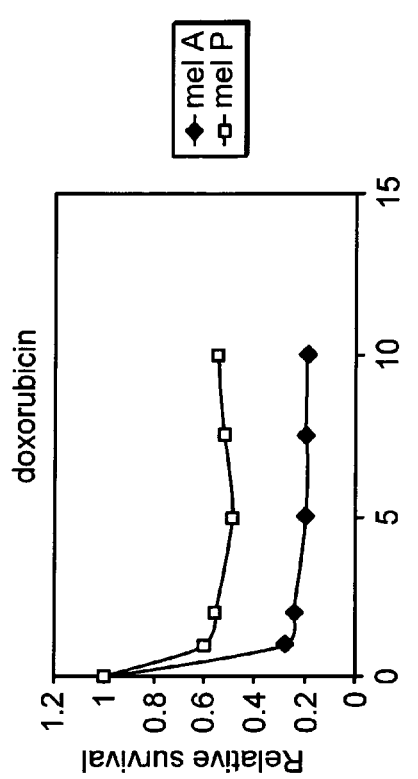
Figure 1O:
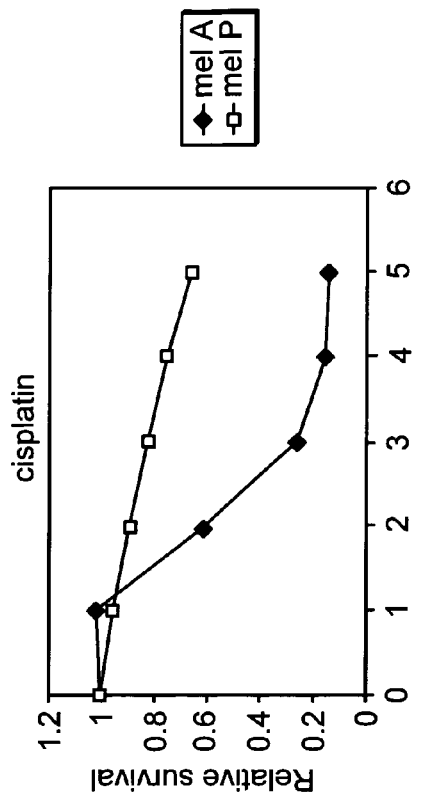
Figure 1P:
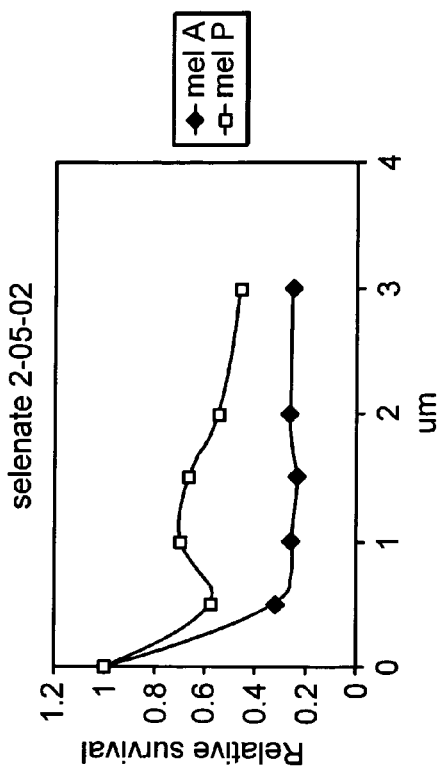
Figure 1Q:
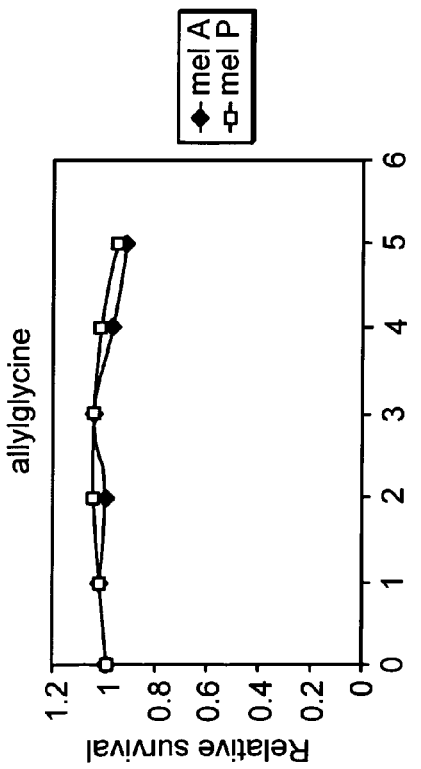
Figure 1R:
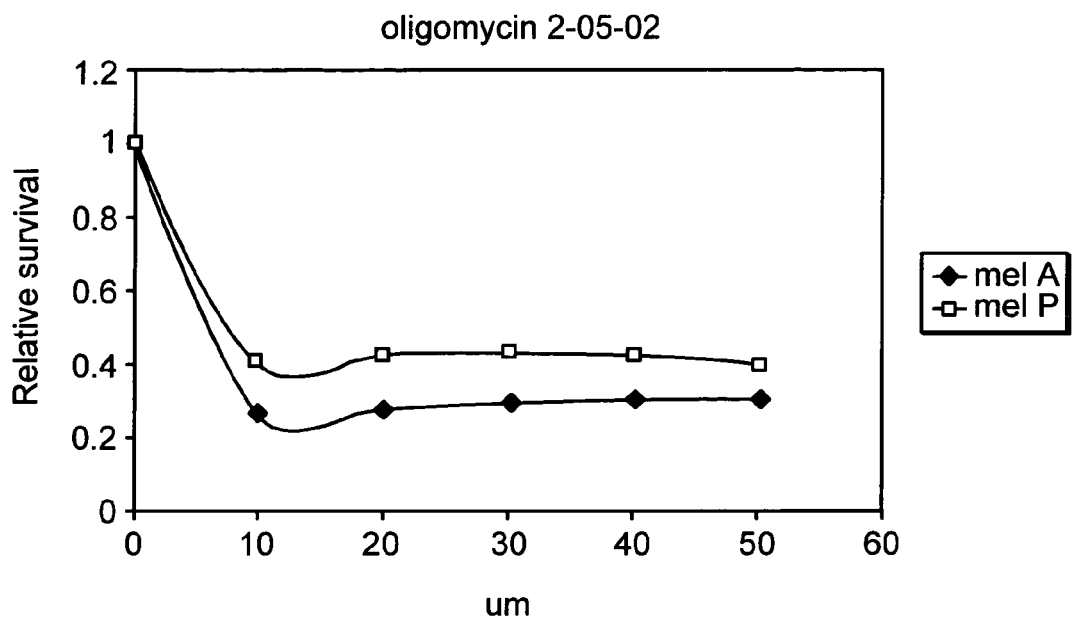
Figure 1S:
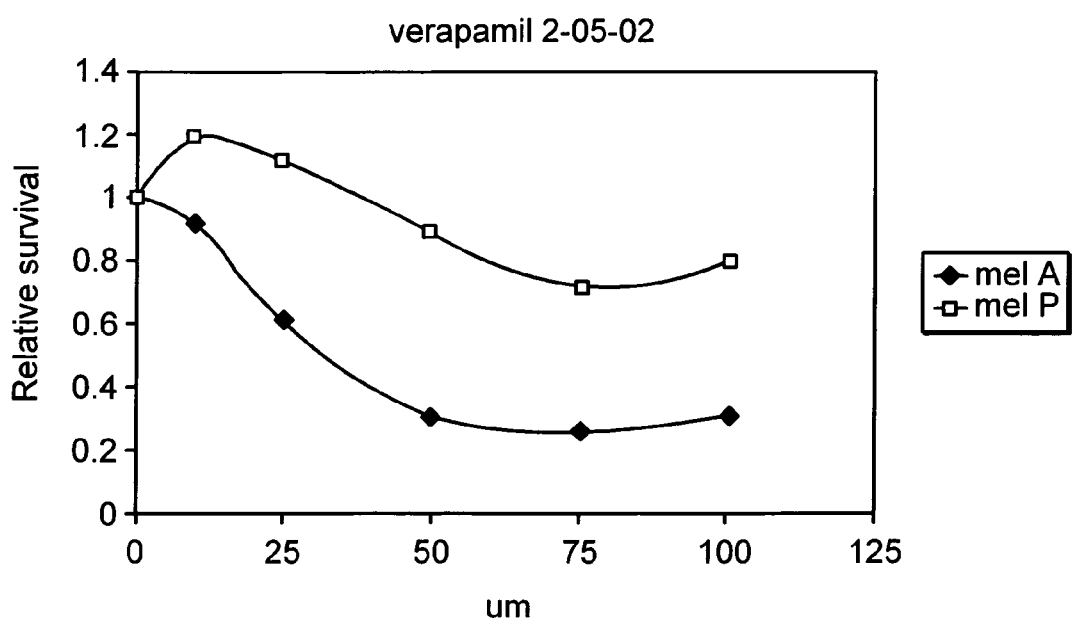
Figure 1U:
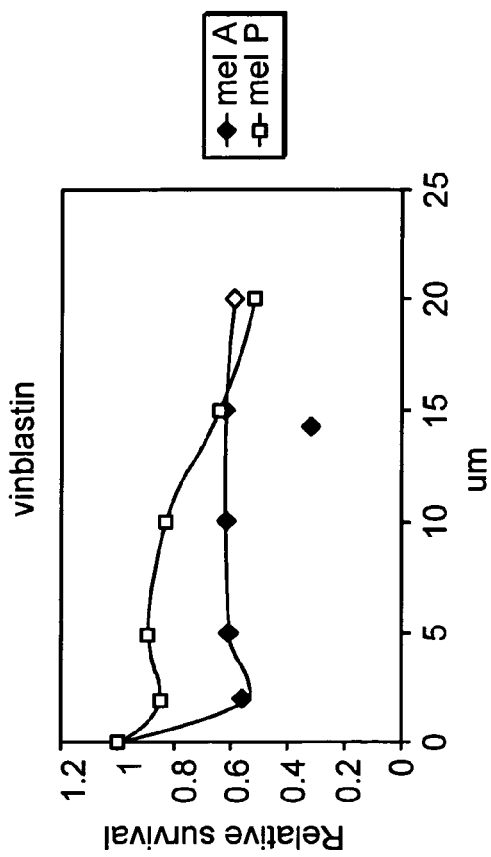
Figure 1V:
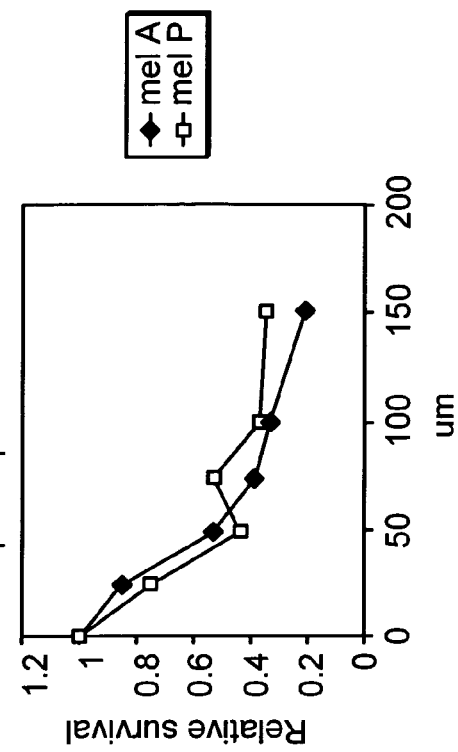
Figure 1T:
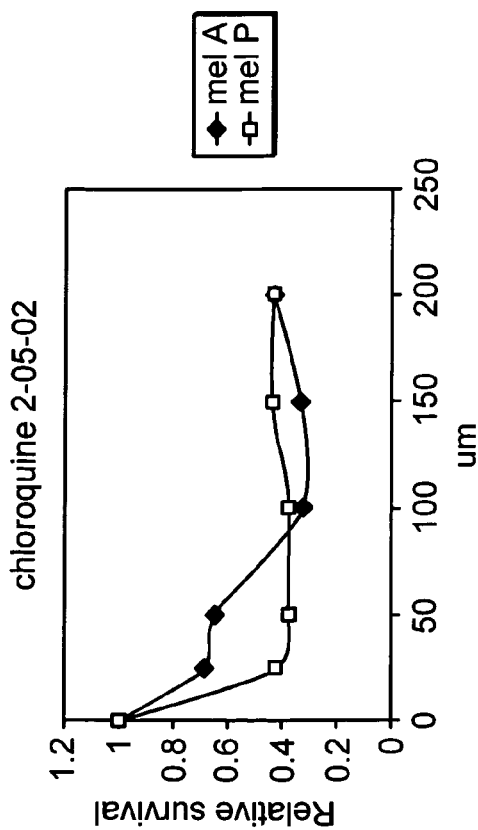
Figure 1X:
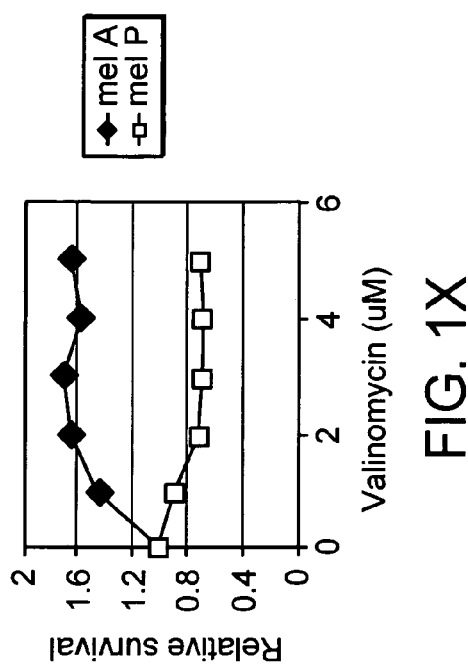
Figure 1W:
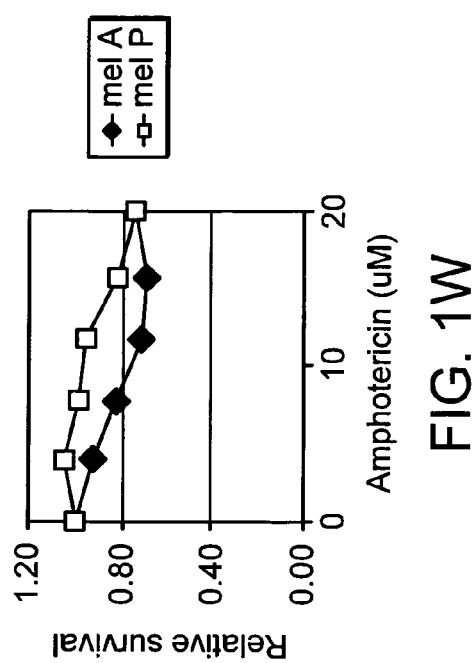
Figure 1Y:
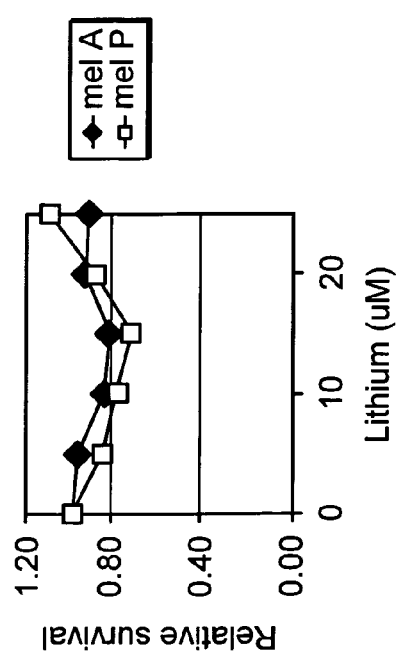

Lemaitre et al., "Specific Antiviral Activity of a Poly(L-lysine)-conjugated Oligodeoxyribonucleotide Sequence Complementary to Vesicular Stomatitis Virus N Protein mRNA Initiation Site", *Proc. Natl. Acad. Sci.* (USA) 84:648-652 (1987).

Letsinger et al., "Cholesteryl-conjugated Oligonucleotides: Synthesis, Properties, and Activity as Inhibitors of Replication of Human Immunodeficiency Virus in Cell Culture", *Proc. Natl. Acad. Sci.* (USA) 86:6553-6556 (1989).

Manga et al., "The *Pink-Eyed Dilution* Gene and the Molecular Pathogenesis of Tyrosinase-Positive Albinism (OCA2)", *J. Dermatol.* 26:738-747 (1999).

Manga et al., "Inverse Correlation Between Pink-Eyed Dilution Protein Expression and Induction of Melanogenesis by Bafilomycin A1", *Pigment Cell Res.* 14:362-367 (2001).

Nordlund et al., eds, *The Pigmentary System: Phsiology and Pathophysiology*, Oxford University, New York (1998) pp. 217-229.

Penninckx, "A Short Review on the Role of Glutathione in the Response of Yeasts to Nutritional, Environmental, and Oxidative Stresses", *Enzyme Microb. Technol.*, 26:737-742 (2000).

Puri, Neelu et al. "Abberrant pH of Melanosomes in Pink-Eyed Dilution (p) mutant melanocytes." *Journal of Investigative Dermatology*, 115(4):607-613 (2000).

Rinchik et al., "A Gene for the Mouse Pink-Eyed dilution Locus and for Human Type II Oculocutaneous Albinism", *Nature.* 361:72-76 (1993).

Scriver et al. *The Matabolic and Molecular Basis of Inherited Disease.* eds, McGraw-Hill Proffesional Publishing, New York, 8th Ed. (2000); pp. 4353-4392.

Staleva, Liliana et al. "Pink-eyed Dilution Protein Modulates Arsenic Sensitivity and Intracellular Glutathione Metabolism." *Molecular Biology of the Cell.*, 13(12): 4206-4220.

Zon, "Oligonucleotide Analogues as Potential Chemotherapeutic Agents", *Pharm. Res.* 5:539-549 (1998).

\* cited by examiner

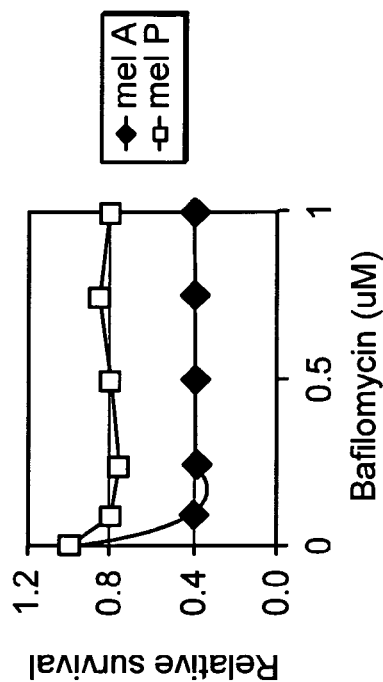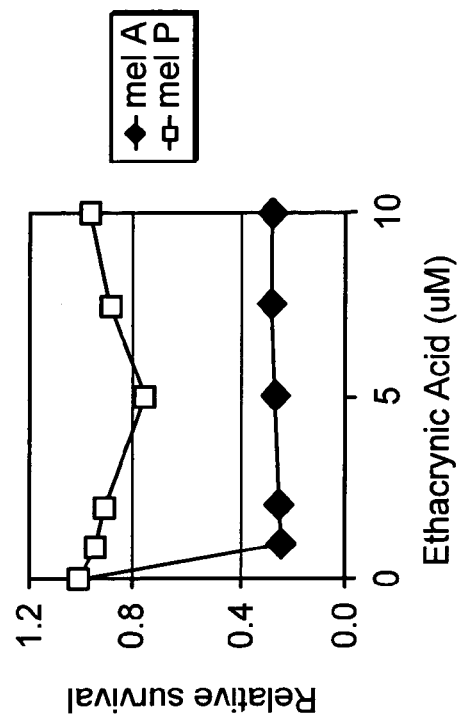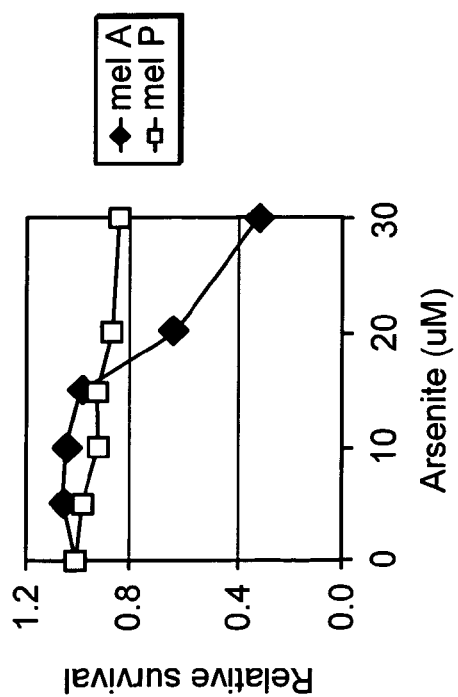

ASSAY FOR MELANOGENESIS

BACKGROUND OF THE INVENTION

1. Field of the Invention

The invention relates to the fields of dermatology, cell biology and cancer. More specifically, the invention relates to the fields of drug discovery, particularly the biology of skin pigmentation, and cancer.

2. Summary of the Related Art

Melanocytes are pigment-producing cells that are principle targets for the treatment of hypo-pigmentation, hyper-pigmentation, and melanoma. The pink-eyed dilution protein (P), which is produced in melanocytes, is necessary for the production of both cutaneous and ocular eumelanin, but the precise function for the P protein is not known. Mutations in the pink-eyed dilution gene result in the most common form of albinism worldwide (*The Metabolic and Molecular Basis of Inherited Disease*. Scriver et al., eds, McGraw-Hill Professional Publishing, New York, 8$^{th}$ Ed. (2000); pp. 4353-4392; ISBN: 0079130356). Affected individuals have hypopigmented skin, hair and eyes (Manga et al., *J. Dermatol.* 26:738-747 (1999)), and are thus at increased risk of developing UV-induced carcinomas (Kromberg et al., *Clin. Genet.* 36:43-52 (1989)).

Several authors have suggested that P protein functions as a tyrosine transporter by pumping tyrosine into the melanosome, where it is converted into melanin by tyrosinase activity (see, e.g., Rinchik et al., *Nature* 361:72-76 (1993)). Contradicting this suggestion, it has been found that tyrosine uptake by melanosomes is virtually the same in P-null and wild-type melanocytes (Gahl et al., *Pigment. Cell. Res.* 8:229-233 (1995)).

This observation has led other authors to hypothesize that P protein is necessary for the transport of some other small molecule, which is necessary for melanogenesis, into melanosomes (Nordlund et al., eds, *The Pigmentary System: Physiology and Pathophysiology*, Oxford University, New York (1998) pp. 217-229) or in controlling the trafficking of melanosomal proteins (Manga et al., *Pigment Cell Res.* 14:362-367 (2001)).

Interestingly, a number of melanoma cell lines fail to express the pink-eyed dilution protein (P)(Id.). Human melanoma is the result of the malignant transformation of melanocytes. The incidence rates for this form of neoplasia have been reported to be increasing by a factor of about 15 over the last 60 years (Gilchrest et al., *New England J. Med.* 340:1341-1348 (1999).

Advanced malignant melanomas have a poor prognosis, particularly since they show increased resistance to many of the currently available chemotherapeutic agents. The mechanisms used by melanomas to escape induction of programmed cell death, or apoptosis, appear to vary. These mechanisms include transport of chemotherapeutic drugs to remove them from their target sites, changes in enzyme activation that affect cellular detoxification, and modulation of the apoptosis pathway itself (Helmbach et al., *Int. J. Cancer* 93:617-622 (2001)).

A variety of treatments for melanoma have been proposed, but the disease is still very difficult to treat in advanced stages. For example, U.S. Pat. No. 5,066,489 describes a combination therapy for the treatment of melanoma; U.S. Pat. No. 5,731,325 describes the treatment of melanomas with thalidomide alone or in combination with other anti-melanoma agents, and U.S. Pat. No. 6,291,196 discloses melanoma and prostate cancer specific antibodies for immunodetection and immunotherapy of these diseases.

Thus, there continues to be a need for improved methods for the treatment of cancer, particularly melanoma.

Many individuals desire to increase or decrease the level of body pigmentation in whole or part. Moreover, medical conditions based on hyper- or hypo-pigmentation also require treatments that are effective at increasing or decreasing the amount of pigment in the skin. A number of compositions are known to lighten skin. For example, hydroquinone is a well-known active substance used for skin de-pigmentation (e.g., see U.S. Pat. No. 6,139,854). Lactoferrin hydrolyzates have been used as a tyrosinase inhibitory agent (e.g., U.S. Pat. Nos. 5,214,028 and 5,389,611), and certain resorcinol derivatives have been used as skin lightening agents (U.S. Pat. No. 6,132,740).

The P protein is one possible target for the treatment of hypo- and hyper-pigmentation. For example, PCT patent publication WO 01/01131 A1 describes methods for the identification of agonists and antagonists of P protein function. These methods are not based on cell viability or cell glutathione content, but rather are based on identifying compounds that affect tyrosinase activity in a P protein dependent fashion or measuring the production of melanin.

There remains a need in the art for more effective and efficient methods of inhibiting melanin production. The need for new and improved methods for lightening skin is evident in view of the cosmetic industry's estimate that the market for skin lighteners worldwide exceeds well over one billion dollars a year. In addition, there is also a need for agents that increase pigmentation for the purpose of providing "safe tanning" or for the treatment of hypopigmentation or the treatment of various forms of albinism. Thus, there is a continuing need for the development of improved agents that limit or inhibit pigmentation in the skin.

BRIEF SUMMARY OF THE INVENTION

The present invention provides methods for the treatment of hyper- and hypo-pigmentation. The invention also provides for the identification of agonists, antagonists, and mimetics of P protein function and pharmaceutical compositions comprising such agonists, antagonists, and mimetics useful for the treatment of hyper- and hypo-pigmentation. Additionally, the invention provides therapeutic methods and agents for the treatment of cancer, particularly of melanomas that do not express the P protein.

It has been determined that cells expressing the P protein are more sensitive to toxins than cells not expressing the P protein. It has also been determined that cells expressing the P protein contain less glutathione than cells that do not express the P protein. Accordingly, the present invention exploits these findings in the methods and compositions disclosed herein.

In one aspect, the invention provides a method of identifying an agent that modifies the function of a P protein. The method comprises (a) contacting control cells expressing a P protein with a toxin and obtaining a measurement of the viability or death of the control cells contacted with the toxin; (b) contacting test cells expressing the P protein with an agent; (c) contacting the agent-contacted test cells with a toxin and obtaining a measurement of the viability or death of the agent-contacted test cells contacted with the toxin; (d) comparing the control cell measurement to the test cell measurement; and (e) identifying the agent as a modifier of P protein function when there is a difference between the control cell measurement and the test cell measurement.

The methods of the invention for the identification of agents that modify P protein function are different from methods for identifying compounds that affect tyrosinase activity in a P protein-dependent fashion or those that measure the production of melanin.

As used herein, the term "agent" refers to any substance that can be applied to cells to achieve the desired effect. An agent can be an inorganic or organic chemical substance. An agent can be an element or a compound or a polymer. For example, an agent can be a small molecule, characterized by a molecular weight of less than about 1,500 g/mole, less than about 1,200 g/mole, or less than about 1,000 g/mole. Useful small molecule drugs, especially those that are orally active are less than about 700 g/mole.

The term "modifies" as used herein refers to an alteration or a change in an inherent characteristic. For example, something that modifies the function of a P protein changes or alters the action for which the protein is specially engaged or used in a cell. "Modified" in this sense refers to an increase or a decrease in the function of the P protein.

As used herein, the term "toxin" refers to a substance that can bring about the death of a cell when the cell is contacted by that substance.

In certain embodiments, the toxin is selected from the group consisting of a metalloid, a metal, a glutathione depleting agent, a chemotherapeutic agent, an ionophore, a vacuolar-type ATPase inhibitor, a microtubule inhibitor, and a DNA interacting agent.

As used herein, the term "metalloid" refers to a nonmetal that can combine with a metal to form an alloy or an element intermediate in properties between the typical metals and nonmetals. Non-limiting examples of metalloids include boron, aluminum, silicon, germanium, arsenic, antimony, tellurium, polonium, astatine, and selenium. In addition, the term is inclusive of derivatives of such elements such as, for example, selenite, arsenite, arsenate, and arsenic trioxide.

The term "metal" is used herein to refer to any of various opaque, fusible, ductile, and typically lustrous substances that are good conductors of electricity and heat, form cations by loss of electrons, and yield basic oxides and hydroxides, especially one that is a chemical element as distinguished from an alloy. Certain metals are referred to as "heavy metals." The term heavy metal refers to any metallic chemical element that has a relatively high density and is toxic, highly toxic or poisonous at low concentrations. Non-limiting examples of heavy metals include mercury, cadmium, arsenic, chromium, thallium, and lead. The term metal as used herein encompasses metal salts, such as, e.g., ferrous sulfate.

The term "glutathione depleting agent" refers to a substance that reduces or eliminates glutathione from a cell that has been contacted by that substance. Non-limiting examples of glutathione depleting agents include ethacrynic acid and buthionine sulfoximine, 1-bromopropane, diethylmaleate, diamide, bromobenzene, and theanine.

As used herein, the term "ionophore" refers to a compound that facilitates transmission of an ion (e.g., calcium) across a lipid barrier (as in a cell membrane) by combining with the ion or by increasing the permeability of the barrier to it. Non-limiting examples of ionophores include monensin, nigericin, and valinomycin.

The term "vacuolar-type ATPase inhibitor" is used herein to refer to any substance that limits or inhibits the activity of a vacuolar-type ATPase. Non-limiting examples of vacuolar-type ATPase inhibitors include bafilomycin A1 and concanamycin.

As used herein, the term "microtubule inhibitor" refers to any substance that impedes the assembly of the protein tubulin to form the microtubule component of the cytoskeleton, mitotic spindle, cilia, or flagella of a cell. Non-limiting examples of microtubule inhibitors include taxol, taxane, vinblastine, vincristine, colchicines, and podophyllotoxin.

As used herein, the term "DNA interacting agent" refers to a substance that binds DNA by way of hydrophilic and/or hydrophobic interaction. Non-limiting examples of DNA interacting agents include doxorubicin, cisplatin and other platinum-containing compounds (such as iproplatin and platinum terpyridine complexes), cyclophosphamide, daunomycin, etoposide, irinotecan, cisplatinol, melphalan, dacarbazine, fotemustine, treosulfan, nimustine, 2-crotonyloxmethyl-cyclohexanone (COMC), amifostine, and pirarubicin.

In other embodiments, the toxin is a metalloid selected from the group consisting of arsenate, arsenic trioxide, and antimony. Alternatively, the toxin is the heavy metal ferrous sulfate. Alternatively, the toxin is a glutathione depleting agent selected from the group consisting of ethacrynic acid and buthionine sulfoximine. In another embodiment, the toxin is a chemotherapeutic agent selected from the group consisting of doxorubicin and vinblastin. In other embodiments, the toxin is the ionophore monensin, the vacuolar-type ATPase inhibitor bafilomycin A1, or the toxin is a DNA interacting agent selected from the group consisting of doxorubicin and cisplatin. In still other embodiments, the toxin is a DNA interacting agent selected from the group consisting of cisplatin and other platinum-containing compounds that are detoxified by glutathione-dependent mechanisms, such as, for example, iproplatin and platinum terpyridine complexes.

Test cells of this aspect of the invention that are contacted with the agent and the toxin are selected from the group consisting of mammalian cells, avian cells, fish cells, nematode cells, insect cells, plant cells, fungal cells, and bacterial cells. In specific embodiments, the test cells are selected from the group consisting of mammalian cells, plant cells, fungal cells, and bacterial cells. In certain embodiments, the test cells are mammalian cells, e.g., human, rat, mouse, hamster, or guinea pig melanocytes, avian melanophores, fish melanophores, nematode cells, insect cells, plant cells, fungal cells, or bacterial cells.

In some embodiments of the method of the invention, control cell and test cell viability are measured. In other embodiments, control cell and test cell death are measured.

In certain embodiments, the agent used to contact the cells is an agonist, antagonist, or mimetic of P protein function. In yet other embodiments, the P protein is a recombinant P protein, or is a mammalian P protein, e.g., a human or mouse P protein.

As used herein, the term "agonist" refers to an agent that increases the activity of a target. By way of non-limiting example, an agonist of P protein function is an agent that increases the activity of P protein. The term "antagonist" refers to an agent that decreases the activity of a target.

In one aspect, the invention provides a method of identifying an agent that is a mimetic of the function of a P protein. The method comprises (a) contacting control cells not expressing a P protein with a toxin and obtaining a measurement of the viability or death of the control cells contacted with the toxin; (b) contacting test cells not expressing the P protein with an agent; (c) contacting the agent-contacted test cells with a toxin and obtaining a measurement of the viability or death of the agent-contacted test cells contacted with the toxin; (d) comparing the control cell measurement to the test cell measurement; and (e) identifying the agent as a P protein-function mimetic when there is a decrease in cell viability or an increase in cell death of test cells versus control cells.

For purposes of the invention, agents that are mimetics of P protein function are compounds that are not P proteins, yet when they are administered to, or incubated with, cells that do not contain P protein, they serve to restore, at least in part, the function of the P protein. Melanogenic cells that do not contain P protein may be cells that do not express P protein transcripts (such as melan-p cells, described herein) or cells that do not express a functional P protein gene product.

In certain embodiments of this method, the test cells are selected from the group consisting of mammalian cells, avian cells, fish cells, nematode cells, insect cells, plant cells, fungal cells, and bacterial cells. In certain embodiments thereof, the test cells are mammalian cells, e.g., human, rat, mouse, hamster, or guinea pig melanocytes, avian melanophores, fish melanophores, nematode cells, insect cells, plant cells, fungal cells, or bacterial cells. In other particular embodiments, cell viability or cell death is measured after contact with the agent.

In still another aspect, the invention provides a method of identifying an agent that modifies P protein function. The method comprises: (a) obtaining a measurement of the amount of glutathione in control cells expressing a P protein; (b) contacting test cells expressing the P protein with an agent; (c) obtaining a measurement of the amount of glutathione in test cells contacted by the agent; (d) comparing the control cell measurement to the test cell measurement; and (e) identifying the agent as a modifier of P protein function when there is a difference between the control cell measurement and the test cell measurement.

In certain embodiments of this method, the test cells are selected from the group consisting of mammalian cells, plant cells, fungal cells, and bacterial cells. In certain embodiments, the test cells are mammalian cells, avian cells, fish cells, nematode cells, insect cells, plant cells, fungal cells, and bacterial cells. In certain embodiments thereof, the test cells are mammalian cells, e.g., human, rat, mouse, hamster, or guinea pig melanocytes, avian melanophores, fish melanophores, nematode cells, insect cells, plant cells, fungal cells, or bacterial cells.

In some embodiments of the method, control cell and test cell viability are measured. In other embodiments, control cell and test cell death are measured.

In certain embodiments of this aspect, the agent is an agonist of P protein function. In other embodiments, the agent is an antagonist of P protein function. In certain embodiments, the P protein is a recombinant P protein, a mammalian P protein, a human P protein, or a mouse P protein.

In another aspect, the invention provides a method of identifying an agent that is a memetic of P protein function. The method comprises: (a) obtaining a measurement of the amount of glutathione in control cells not expressing a P protein; (b) contacting test cells that do not express the P protein with an agent; (c) obtaining a measurement of the amount of glutathione in agent-contacted test cells; (d) comparing the control cell measurement to the test cell measurement; and (e) identifying the agent as P protein-function mimetic when the test cell measurement is lower than the control cell measurement.

In certain embodiments of this method, the test cells are selected from the group consisting of mammalian cells, plant cells, fungal cells, and bacterial cells. In certain embodiments, the test cells are mammalian cells, avian cells, fish cells, nematode cells, insect cells, plant cells, fungal cells, and bacterial cells. In certain embodiments thereof, the test cells are mammalian cells, e.g., human, rat, mouse, hamster, or guinea pig melanocytes, avian melanophores, fish melanophores, nematode cells, insect cells, plant cells, fungal cells, or bacterial cells.

The invention also provides in another aspect a method of identifying an agent that modifies the function of a P protein. The method comprises: (a) contacting control fungal cells expressing a P protein with selenite and obtaining a measurement of the amount of red pigment formation in the control fungal cells; (b) contacting test fungal cells expressing the P protein with an agent; (c) contacting the agent-contacted test fungal cells with selenite, and obtaining a measurement of the amount of red pigment formation in the toxin- and agent-contacted test fungal cells; (d) comparing the control cell measurement to the test cell measurement; and (e) identifying the agent as a modifier of P protein function when there is a difference between the control cell measurement and the test cell measurement.

In certain embodiments of this aspect of the invention, the fungal cells are *Saccharomyces cerevisiae* or *Schizosaccharomyces pombe*.

In another aspect, the invention provides a method of stimulating melanogenesis, which is useful for the treatment of, e.g., hypopigmentation or type 2 albinism. The method comprises contacting a melanocyte with an agonist of P protein function. In this aspect, the agonist of P protein function identified by the method comprising: (a) contacting control cells expressing a P protein with a toxin, and obtaining a measurement of the viability or death of the toxin-contacted control cells; (b) contacting test cells expressing the P protein with an agent; (c) contacting the agent-contacted test cells with a toxin, and obtaining a measurement of the viability or death of the toxin- and agent-contacted test cells; (d) comparing the control cell measurement to the test cell measurement; and (e) identifying the agent as an agonist of P protein function when test cell viability is lower, or test cell death is higher, than the corresponding control cell measurement.

As used herein, the term "melanogenesis" refers to the process of the formation of the pigment melanin, and the term "stimulating melanogenesis" means to bring about or increase this process in a cell. The effect of stimulating melanogenesis is to increase the production of melanin, thereby darkening or "tanning" the skin.

In another aspect, the invention provides for methods of stimulating melanogenesis by way of administering a mimetic of P protein function identified by one of the methods of the invention.

In yet another aspect, the invention provides a method of inhibiting melanogenesis, which is useful in the treatment of disorders of over pigmentation such as, e.g., nevi. The method comprises contacting a melanocyte with an antagonist of P protein function. In this aspect, the antagonist of P protein function is identified by the method comprising: (a) contacting control cells expressing a P protein with a toxin, and obtaining a measurement of the viability or death of the contacted control cells; (b) contacting test cells expressing the P protein with an agent; (c) contacting the agent-contacted test cells with a toxin, and obtaining a measurement of the viability or death of the toxin- and agent-contacted test cells; (d) comparing the control cell measurement to the test cell measurement; and (e) identifying the agent as an antagonist of P protein function when the measurement of test cell viability is higher, or the measurement of test cell death is lower, than the corresponding control cell measurement.

In still another aspect, the invention provides a pharmaceutical composition comprising a pharmaceutically acceptable carrier and an agonist of P protein function. In this aspect, the agonist of P protein function is identified by the method comprising: (a) contacting control cells expressing a P protein with a toxin, and obtaining a measurement of the viability or death of the toxin-contacted control cells; (b) contacting test cells expressing the P protein with an agent; (c) contacting the agent-contacted test cells with a toxin, and obtaining a measurement of the viability or death of the toxin- and agent-contacted test cells; (d) comparing the control cell measurement to the test cell measurement; and (e) identifying the agent as an agonist of P protein function when the measurement of test cell viability is lower, or the measurement of test cell death is higher, than the corresponding control cell measurement.

In another aspect, the invention provides a pharmaceutical composition comprising a pharmaceutically acceptable carrier and an antagonist of P protein function. In this aspect, the antagonist of P protein function is identified by the method comprising: (a) contacting control cells expressing a P protein with a toxin, and obtaining a measurement of the viability or death of the toxin-contacted control cells; (b) contacting test cells expressing the P protein with an agent; (c) contacting the agent-contacted test cells with a toxin, and obtaining a measurement of the viability or death of the toxin- and agent-contacted test cells; (d) comparing the control cell measurement to the test cell measurement; and (e) identifying the agent as an antagonist of P protein function when the measurement of test cell viability is higher, or the measurement of test cell death is lower, than the corresponding control cell measurement.

In still another aspect, the invention provides a pharmaceutical composition comprising a pharmaceutically acceptable carrier and a mimetic of P protein function. In this aspect, the mimetic of P protein function is identified by the method comprising: (a) contacting control cells not expressing a P protein with a toxin and obtaining a measurement of the viability or death of the control cells contacted with the toxin; (b) contacting test cells not expressing the P protein with an agent; (c) contacting the agent-contacted test cells with a toxin and obtaining a measurement of the viability or death of the agent-contacted test cells contacted with the toxin; (d) comparing the control cell measurement to the test cell measurement; and (e) identifying the agent as a P protein-function mimetic when there is a decrease in cell viability or an increase in cell death for test cells versus control cells.

In yet another aspect, the invention provides a method of stimulating melanogenesis, which is useful for the treatment of, e.g., hypopigmentation or type 2 albinism. The method comprises contacting a melanocyte with an agonist of P protein function. In this aspect, the agonist of P protein function is identified by the method comprising: (a) obtaining a measurement of the amount of glutathione in control cells expressing a P protein; (b) contacting test cells expressing the P protein with an agent; (c) obtaining a measurement of the amount of glutathione in agent-contacted test cells; (d) comparing the control cell measurement to a test cell measurement; and (e) identifying the agent as an agonist of P protein function if the test cell measurement is lower than the control cell measurement.

In another aspect, the invention provides a method of inhibiting melanogenesis, which is useful in the treatment of disorders of over pigmentation such as, e.g., nevi. The method comprises contacting a melanocyte with an antagonist of P protein function. In this aspect, the antagonist of P protein function is identified by the method comprising: (a) obtaining a measurement of the amount of glutathione in control cells expressing a P protein; (b) contacting test cells expressing the P protein with an agent; (c) obtaining a measurement of the amount of glutathione in agent-contacted test cells; (d) comparing the control cell measurement to a test cell measurement; and (e) identifying the agent as an antagonist of P protein function if the test cell measurement is higher than the control cell measurement.

In still another aspect, the invention provides a pharmaceutical composition comprising a pharmaceutically acceptable carrier and an agonist of P protein function. In this aspect, the agonist of P protein function is identified by the method comprising: (a) obtaining a measurement of the amount of glutathione content obtained from control cells expressing a P protein; (b) contacting test cells expressing the P protein with an agent; (b) obtaining a measurement of the amount of glutathione in test cells contacted by the agent; (c) comparing the control cell measurement to a test cell measurement; and (d) identifying the agent as an agonist of P protein function if the test cell measurement is lower than the control cell measurement.

In another aspect, the invention provides a pharmaceutical composition comprising a pharmaceutically acceptable carrier and an antagonist of P protein function. In this aspect, the antagonist of P protein function is identified by the method comprising: (a) obtaining a measurement of the amount of glutathione in control cells expressing a P protein; (b) contacting test cells expressing the P protein with an agent; (c) obtaining a measurement of the amount of glutathione in agent-contacted test cells; (d) comparing the control cell measurement to a test cell measurement; and (e) identifying the agent as an antagonist of P protein function if the test cell measurement is higher than the control cell measurement.

In still another aspect, the invention provides a pharmaceutical composition comprising a pharmaceutically acceptable carrier and a mimetic of P protein function. In this aspect, the mimetic of P protein function is identified by the method comprising: (a) obtaining a measurement of the amount of glutathione in control cells not expressing a P protein; (b) contacting test cells that do not express the P protein with an agent; (c) obtaining a measurement of the amount of glutathione in agent-contacted test cells; (d) comparing the control cell measurement to the test cell measurement; and (e) identifying the agent as P protein-function mimetic when the test cell glutathione measurement is lower than the control cell glutathione measurement.

In yet another aspect, the invention provides a method of treating a patient having cancer. In this method, a cancer cell is contacted with an agonist or mimetic of P protein function, the agonist or mimetic of P protein function identified by any one of the methods of the invention. The cancer cell is then contacted with a chemotherapeutic agent. In various embodiments thereof, the cancer treated is selected from the group consisting of liver cancer, pancreatic cancer, lung cancer, colon cancer, intestinal cancer, stomach cancer, brain cancer, a leukocytic cancer, bone cancer, ovarian cancer, testicular cancer, and melanoma cancer.

In another aspect, the invention provides a method of increasing the sensitivity of a cell that does not express a P protein to a toxin. The method comprises: (a) introducing into the cell a nucleic acid molecule encoding the P protein that enables the expression of the P protein in the cell; and (b) expressing the P protein in the cell at a sufficient level to increase sensitivity of the cell to the toxin.

In another aspect, the invention provides a method of increasing the sensitivity to a toxin of a cell that does not express a P protein. The method comprises contacting the cell with a P protein mimetic.

In another aspect, the compositions and pharmaceutical compositions of the invention may be provided in the form of a kit. Kits of the invention comprise one or more specific compositions and/or pharmaceutical compositions of the invention that modify P protein function or that are useful as therapeutic treatment for melanoma, in a container.

BRIEF DESCRIPTION OF THE DRAWINGS

The foregoing and other objects of the present invention, the various features thereof, as well as the invention itself may be more fully understood from the following description, when read together with the accompanying drawings in which:

FIG. 1A is a graphic presentation demonstrating the effect of arsenate on cell viability of cells that express, and cells that do not express, the P protein.

FIG. 1B is a graphic presentation demonstrating the effect of arsenic trioxide on cell viability of cells that express, and cells that do not express, the P protein.

FIG. 1C is a graphic presentation demonstrating the effect of antimony on cell viability of cells that express, and cells that do not express, the P protein.

FIG. 1D is a graphic presentation demonstrating the effect of iron sulfate ($FeSO_4$) on cell viability of cells that express, and cells that do not express, the P protein.

FIG. 1E is a graphic presentation demonstrating the effect of vinblastin on cell viability of cells that express, and cells that do not express, the P protein.

FIG. 1F is a graphic presentation demonstrating the effect of carbonyl cyanide p-trifluoromethoxyphenylhydrazone (FCCP) on cell viability of cells that express, and cells that do not express, the P protein.

FIG. 1G is a graphic presentation demonstrating the effect of primaquine on cell viability of cells that express, and cells that do not express, the P protein.

FIG. 1H is a graphic presentation demonstrating the effect of cycloheximide acid on cell viability of cells that express, and cells that do not express, the P protein.

FIG. 1I is a graphic presentation demonstrating the effect of bafilomycin on cell viability of cells that express, and cells that do not express, the P protein.

FIG. 1J is a graphic presentation demonstrating the effect of arsenite on cell viability of cells that express, and cells that do not express, the P protein.

FIG. 1K is a graphic presentation demonstrating the effect of ethacrynic acid on cell viability of cells that express, and cells that do not express, the P protein.

FIG. 1L is a graphic presentation demonstrating the effect of cadmium on cell viability of cells that express, and cells that do not express, the P protein.

FIG. 1M is a graphic presentation demonstrating the effect of buthionine sulfoximine (BSO) on cell viability of cells that express, and cells that do not express, the P protein.

FIG. 1N is a graphic presentation demonstrating the effect of selenate on cell viability of cells that express, and cells that do not express, the P protein.

FIG. 1O is a graphic presentation demonstrating the effect of doxorubicin on cell viability of cells that express, and cells that do not express, the P protein.

FIG. 1P is a graphic presentation demonstrating the effect of allylglycine on cell viability of cells that express, and cells that do not express, the P protein.

FIG. 1Q is a graphic presentation demonstrating the effect of cisplatin on cell viability of cells that express, and cells that do not express, the P protein.

FIG. 1R is a graphic presentation demonstrating the effect of oligomycin on cell viability of cells that express, and cells that do not express, the P protein.

FIG. 1S is a graphic presentation demonstrating the effect of verapamil on cell viability of cells that express, and cells that do not express, the P protein.

FIG. 1T is a graphic presentation demonstrating the effect of chloroquine on cell viability of cells that express, and cells that do not express, the P protein.

FIG. 1U is a graphic presentation demonstrating the effect of viblastin on cell viability of cells that express, and cells that do not express, the P protein.

FIG. 1V is a graphic presentation demonstrating the effect of primaquine on cell viability of cells that express, and cells that do not express, the P protein.

FIG. 1W is a graphic presentation demonstrating the effect of amphotericin on cell viability of cells that express, and cells that do not express, the P protein.

FIG. 1X is a graphic presentation demonstrating the effect of valinomycine on cell viability of cells that express, and cells that do not express, the P protein.

FIG. 1Y is a graphic presentation demonstrating the effect of lithium on cell viability of cells that express, and cells that do not express, the P protein.

FIG. 2 is a graphic presentation showing the level of glutathione in cells that express the protein, and the level in cells that do not express, the P protein.

FIG. 3A is a reproduction of a photograph of yeast colony size after exposure to arsenate, arsenic trioxide, and antimony for cells expressing and not expressing a P protein.

FIG. 3B is a reproduction of a photograph demonstrating yeast colony size and red precipitate formation in cells exposed to selenite for cells expressing and not expressing a P protein.

DETAILED DESCRIPTION OF THE PREFERRED EMBODIMENTS

The patents and publications cited herein reflect the level of knowledge in the art and are hereby incorporated by reference in their entirety. Any conflict between any teaching of such references and this specification shall be resolved in favor of the latter.

The invention utilizes techniques and methods common to the fields of molecular biology, genetics and microbiology. Useful laboratory references for these types of methodologies are readily available to those skilled in the art. See, for example, *Molecular Cloning, A Laboratory Manual,* 3rd ed., Sambrook et al., Eds. (2001), Cold Spring Harbor Laboratory Press (ISBN: 0-879-69576-5); *Current Protocols In Molecular Biology*, Ausubel et al., Eds. (1993), John Wiley and Sons, Inc. (ISBN: 0-471-30661-4); *PCR Applications: Protocols for Functional Genomics*, Innis et al., Eds. (1999), Cold Spring Harbor Press (ISBN: 0-123-72186-5).

The invention disclosed herein provides knowledge heretofore unknown in the scientific, pharmaceutical, or medical communities. It has been determined that cells expressing P protein, the expression of which is critical for the production of melanin in melanocytes, are more sensitive to toxins than cells that do not express P protein. The invention also establishes that cells expressing the P protein have a lower amount of glutathione than cells that do not express the P protein. These observations provide the basis for the methods and compositions disclosed by the invention.

Given the importance of the P protein in melanogenesis, the identification of agents that are antagonists or agonists of P protein is useful for the treatment of hypo- and hyper-pigmentation. Measurement of toxin sensitivity of cells expressing P protein is also useful in the design of and the application of therapeutic treatments.

The invention provides methods to identify agents that modify or change the function of P protein. Some methods of the invention are based on assays that measure cell viability and/or cell death. For example, control cells expressing P protein are contacted with one or more toxins, and a measurement of cell death and/or cell viability is then obtained. Test cells that also express the P protein are first exposed to an agent and then exposed to a toxin or toxins. After toxin exposure, a measurement of cell death and/or cell viability is obtained for these test cells. A comparison between the control cell and test cell measurement of cell death and/or cell viability is obtained to determine if the agent is a modifier of P protein function. An agent is identified as a modifier of P protein function if the test cells are more or less sensitive to the toxin(s) than the control cells, which were not exposed to the agent.

As will be appreciated by those skilled in the art, cells selected for the methods of the invention can be of any type. Typically, test cells and control cells are identical in origin and/or genotype. By way of non-limiting example, cells used in the methods of the invention can be eukaryotic or prokaryotic. More specifically, cells utilized by the invention can be mammalian, plant, fungal, or bacterial cells.

In one example, the cells utilized are melanocytes. In another example, the cells utilized in the methods of the invention are not melanocytes. More specifically, cells utilized by the methods of the invention need not be melanocytes expressing the P protein, but may be other cell types, eukaryotic or prokaryotic, that express the P protein. Typically, expression of the P protein in non-melanocyte cells is the result of expression in these cells by recombinant means.

By way of non-limiting example, any cell type can be used in the methods of the invention that sufficiently expresses a P protein after introduction into the cell of the appropriate P protein encoding gene sequence, either extrachromasomally or by way of integration into the genome. Gene sequences encoding a P protein can be synthetic sequences, based on an appropriate template, made by chemical synthesis means. Alternatively, such gene sequences can be obtained from a biological source, such as from a host cell carrying a cloned cDNA or genomic sequence, or P protein encoding gene sequences can be produced enzymatically, e.g., by reverse transcription or polymerase chain reaction. P protein-encoding genes are known in the art, see, for example, Rinchik et al., *Nature* 361:72-76 (1993), and the MEDLINE database at accession nos., for example, NM_000275 and U19152 for the human gene.

P protein-encoding gene sequences expressed by cells used in the methods of the invention can be ribonucleic acid (RNA) or deoxyribonucleic acid (DNA) sequences. The introduction of RNA or DNA sequences into the selected cell can be by any means known to those skilled in the art. By way of non-limiting example, P protein encoding DNA sequences can be introduced into a cell by way of transformation, calcium-mediated transduction, or transfection. The DNA sequences can be optionally associated with an appropriate vector sequence that itself comprises the appropriate regulatory sequences for transcription and translation of the protein in the cell. RNA sequences encoding P protein according to the invention can be introduced by way of any suitable vector, e.g., a liposome or any DNA or RNA vector comprising the appropriate regulatory sequences for transcription and translation in a cell, e.g., T3 or T7 RNA polymerase promoter sequence.

Expression cassettes are typically used to express heterologous genes in the chosen cell. Each expression cassette contains regulatory sequences designed to express, for example, a P protein-encoding gene. For expression in prokaryotic cells, preferably each coding sequence found in the expression cassette is operatively linked to at least one regulatory sequence, i.e., a promoter sequence. By "Operatively linked" means that the regulatory sequence functions to regulate the coding sequence (e.g., controls the timing or amount of expression of the coding sequence, determines initiation or termination of transcription or translation, or affects message stability). For expression in eukaryotic cells, preferably each coding sequence found in the expression cassette is operatively linked to at least two regulatory sequences, i.e., a promoter and a poly A adenylation sequence. Each expression cassette is operatively linked to the polynucleotide sequence of a vector. Each vector preferably contains polynucleotide sequences that allow for its selection, replication, and maintenance in transfected cells, either as an autonomous extrachromosomal element, or as an integrated component of one or more chromosomes in the transfected cells. Vectors containing expression cassettes that can be adapted to express almost any coding sequence are well known in the art and commercially available. Non-limiting examples of such vectors are the pcDNA vectors, which are available from Invitrogen (San Diego, Calif.).

Any promoter that facilitates a sufficiently high rate of expression can be used in the expression cassette. The promoter can be constitutive or inducible. See, e.g., Resendez et al., *Mol. Cell Biol.* 8:4579-4584 (1988); and Chang et al., *Proc. Natl. Acad. Sci. USA* 84:680-684 (1987), which describe inducible promoters. The choice of the promoter depends on what cell type is used in the screen and the desired level of expression of the heterologous genes encoding the P protein. See, e.g., Gossen et al., *Science* 268:1766-1769 (1995); Gossen and Bujard, *Proc. Natl. Acad. Sci. USA* 89:5547-5551 (1992); and U.S. Pat. Nos. 5,851,984; 5,849,997; 5,827,687; 5,811,260; 5,789,215; 5,665,578; 5,512,483; 5,302,517; 4,959,313; and 4,935,352, which describe useful promoter sequences.

Further non-limiting examples of promoter sequences and elements include the SV40 early promoter region (Bernoist and Chambon, *Nature* 290:304-310 (1981)), the promoter contained in the 3' long terminal repeat of Rous sarcoma virus (Yamamoto, et al., *Cell* 22:787-797 (1980)), the herpes thymidine kinase promoter (Wagner et al., *Proc. Natl. Acad. Sci.* (*USA*) 78:1441-1445 (1981)), the regulatory sequences of the metallothionein gene (Brinster et al., *Nature* 296:39-42 (1982)); prokaryotic expression vectors such as the β-lactamase promoter (Villa-Kamaroff, et al., *Proc. Natl. Acad. Sci.* (*USA*) 75:3727-3731 (1978)), and the tac promoter (DeBoer, et al., *Proc. Natl. Acad. Sci.* (*USA*) 80:21-25 (1983)); see also [AUTHORS?], *Scientific American,* 242: 74-94 (1980); plant expression vectors comprising the nopaline synthetase promoter region (Herrera-Estrella et al., *Nature* 303:209-213) or the cauliflower mosaic virus 35S RNA promoter (Gardner, et al., *Nucl. Acids Res.* 9:2871 (1981)), and the promoter of the photosynthetic enzyme ribulose biphosphate carboxylase (Herrera-Estrella et al., *Nature* 310:115-120 (1984)); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: the elastase I gene control region, which is active in pancreatic acinar cells (Swift et al. *Cell* 38:639-646 (1984); Ornitz et al., *Cold Spring Harbor Symp. Quant. Biol.* 50:399-409 (1986); MacDonald, *Hepatol.* 7:425-515 (1987)); the insulin gene control region, which is active in pancreatic beta cells (Hanahan, *Nature* 315:115-122 (1985)); the immunoglobulin gene control region, which is active in lymphoid cells (Grosschedl et al., *Cell* 38:647-658 (1984); Adames et al., *Nature* 318:533-538 (1985); Alexander et al., *Mol. Cell. Biol.* 7:1436-1444 (1987)); the mouse mammary tumor virus control region, which is active in testicular, breast, lymphoid and mast cells (Leder et al., *Cell* 45:485-495 (1986)); the albumin gene control region, which is active in liver (Pinkert et al., *Genes and Devel.* 1:268-276 (1987)); the alpha-fetoprotein gene control region, which is active in liver (Krumlauf et al., *Mol. Cell. Biol.* 5:1639-1648 (1985); Hammer et al., *Science* 235:53-58 (1987)); the alpha 1-antitrypsin gene control region, which is active in the liver (Kelsey et al., *Genes and Devel.* 1:161-171 (1987)); the beta-globin gene control region, which is active in myeloid cells (Mogram et al., *Nature* 315:338-340 (1985)); Kollias et al., *Cell* 46:89-94 (1986)); the myelin basic protein gene control region, which is active in oligodendrocyte cells in the brain (Readhead et al., *Cell* 48:703-712 (1987)); the myosin light chain-2 gene control region, which is active in skeletal muscle (Sani, *Nature* 314:283-286 (1985)); and the gonadotropic releasing hormone gene control region, which is active in the hypothalamus (Mason et al., *Science* 234:1372-1378 (1986)).

Another regulatory element that can be used in the expression cassette for eukaryotic cell expression is a poly A sequence (or poly A signal), which should be capable of efficiently inducing polyadenylation of a transcript specific for the coding sequence to which the poly A sequence is operatively linked. See, e.g., U.S. Pat. Nos. 5,861,290; 5,851,984; 5,840,525 and 5,627,033, which discuss poly A sequences.

In another non-limiting embodiment, the expression cassette used according to the present invention may further comprise an enhancer element, a 5' or 3' untranslated sequence (or region), one or more introns, a sequence that regulates RNA stability, or a combination of more than one of these elements. Any sequence that falls into any of these categories can be used in the vector of the present invention. See U.S. Pat. Nos. 5,861,290; 5,851,984; 5,840,525; 5,681,744 and 5,627,033, which discuss these regulatory elements. The term "5' untranslated sequence" refers to the sequence of an mRNA molecule between the transcription initiation site and the translation initiation site. The term "3' untranslated sequence" refers to the sequence of an mRNA molecule between the translation termination site and the poly A tail.

The heterologous P protein encoding genes used in these assays are typically introduced into the chosen cells by transfection, transduction, transformation, or any other suitable technique known in the art. For example, electroporation, calcium phosphate coprecipitation, microinjection, lipofection, etc., can be used. See, e.g., U.S. Pat. Nos. 5,814,618 and 5,789,215, which describe transfection methods. The cells that take up the heterologous gene or genes, either through integration into their genome or by maintenance as part of an extrachromosomal element, are then preferably selected by standard techniques. Thus, a selectable marker can be included in the vector that allows a cell that has the marker, and thus cells that contain the vector and the heterologous gene or genes, to be isolated from cells that do not have the marker. Whether a selectable marker is necessary to prepare the cells used in these assays depends on the particular method by which the vector is introduced into the cells. For example, if the vector is introduced into the cells via microinjection, a selectable marker may be less useful than if electroporation is used because the transformation frequency tends to be higher for microinjection. For example, the marker can enable a cell to grow under selective conditions, i.e. conditions under which the cell could not grow if it did not have the marker (e.g., the neomycin resistance gene and the hypoxanthine phosphoribosyltransferase gene). A marker can also provide another means by which to identify the cell that took up the heterologous polynucleotide molecule or vector (e.g., by preferential staining). See, e.g., U.S. Pat. Nos. 5,851,984 and 5,789,215, which describe selectable markers.

As disclosed previously, the invention provides that cells expressing a P protein are more sensitive to toxins. Toxins utilized by the methods of the invention can be selected from a wide variety of chemicals or compounds that collectively operate by diverse mechanisms to injure a cell or bring about its death. By way of non-limiting example, such toxins can be a metalloid, a heavy metal, a glutathione-depleting agent, a chemotherapeutic agent, an ionophore, a vacuolar-type ATPase inhibitor, a microtubule inhibitor, or a DNA interacting agent.

Certain methods of the invention utilize assays designed to measure cell viability and/or cell death. As known to those skilled in the art, many assays are available for the measurement of cell viability and/or cell death. For example, cells can be stained with a vital dye, e.g., trypan blue, and examined by low-power microscopy to determine cell viability. Commercially available assay kits can also be used to measure cell viability and/or cell death. For example, such kits include the Wallac CytoLux kit (PerkinElmer Life Sciences, Boston, Mass.) or the CellTiter-Glo™ Luminescent Cell Viability Assay (Promega Corp., Madison, Wis.).

Certain methods of the invention identify mimetics of P protein function. For example, control cells that do not express a P protein are exposed to a toxin and a measurement of cell viability/cell death is obtained. Test cells not expressing the P protein are also exposed to the toxin after being contacted with an agent to be tested for P protein mimetic characteristics. A measurement of cell viability/cell death for the test cells under these conditions is then compared to the measurement obtained for the control cells, which do not express the P protein and which were exposed to a toxin. An increase in cell viability or a decrease in cell death for the test cells is indicative that the agent tested is a mimetic of P protein function.

The methods of screening for compounds that modify P protein function described above can be used to test individual compounds or numbers of compounds contemporaneously. High-throughput methods of screening, as known in the art, are useful.

For purposes of the present invention, the term "high-throughput method of screening" is defined as a method of screening that allows for large numbers of compounds to be tested concurrently. Each or all of the steps in screening compounds that modify P protein function are amenable to high throughput methods of screening for candidate compounds. Preferably, the high-throughput methods of screening are partially or fully automated, reducing the amount of attention required to test each compound. For example, increased or decreased sensitivity to toxins, or the total level of glutathione, can be detected easily in the formats (such as, e.g., 96 well plates) typically used in high-throughput methods of screening.

High-throughput methods of screening are well known in the art and can be performed in any of a number of formats. Laboratory automation, including robotics technology, can significantly decrease the time necessary to screen large numbers of compounds, and is commercially available from, for example, Tecan (Research Triangle Park, N.C.), Scitec Laboratory Automation SA (Lausanne, Switzerland), Rosys (New Castle, Del.), Rixan Associates Inc. (Dayton, Ohio), CRS Robotics (Burlington, Ontario Canada), Fanuk Robotics, and Beckman-Coulter Sagian (Indianapolis, Ind.), to name just a few companies.

Glutathione (γ-glutamyl-cysteinyl glycine) is the most abundant, non-protein thiol compound present in almost all eukaryotic cells. Physiological values for the concentration of intracellular glutathione generally range from 1 mM to 10 mM. Glutathione plays numerous roles in the cell, including protection from oxidative stress, drug detoxification, maintenance of the redox status, assisting in protein folding and storage of sulfur. The relative stability of the tripeptide, due to the γ-glutamyl linkage, and the strong nucleophilic center in the central cysteine residue, may account for these important functions (reviewed in Penninckx, *Enzyme Microb. Technol.* 26:737-742 (2000)).

The invention provides that cells expressing the P protein contain less glutathione than cells that do not express the P protein. Thus, the invention provides methods for the identification of agents that modify P protein function by monitoring the amount of glutathione content in cells that express P protein and are exposed to the agent.

For example, a measurement of the amount of glutathione in control cells expressing a P protein is obtained. Test cells, which also express the P protein, are first exposed to an agent. After a sufficient period of time, e.g., between 30 minutes and 72 hours, a measurement of the amount of glutathione present in test cells exposed to the agent is obtained. The measurements of glutathione in control cells and in test cells are then compared. Any change in the measurement obtained from test cells as compared to the measurement from control cells is an indication that the agent being tested is a modifier of P protein function. For example, an increase in the amount of glutathione in P protein-expressing cells exposed to an agent indicates that the agent is an antagonist of P protein function, since such cells have more glutathione than expected for cells expressing the P protein, and a decrease in the amount of glutathione in P protein-expressing cells exposed to an agent indicates that the agent is an agonist of P protein function, since such cells have less glutathione than expected for cells expressing the P protein.

Other methods of the invention identify mimetics of P protein function. For example, the glutathione content of control cells that do not express a P protein is obtained. Test cells, which also do not express the P protein, are exposed to an agent to be tested for P protein mimetic characteristics. A measurement of glutathione content for the test cells under these conditions is then compared to the measurement obtained for the control cells, which do not express the P protein. A decrease in level of glutathione in test cells is indicative that the agent tested is a mimetic of P protein function.

As will be appreciated by those skilled in the art, a variety of cells that produce glutathione can be used in the methods of the invention. For example, such cells can be prokaryotic or eukaryotic. More specifically, cells utilized in this method can be mammalian, e.g., human, mouse, rat, or guinea pig, avian, fish, nematode, insect, plant, fungal, or bacterial cells.

In one example, the cells utilized in the method are melanocytes. Alternatively, the cells utilized in the methods of the invention are not melanocytes. More specifically, cells utilized in the methods of the invention need not be melanocytes expressing the P protein, but may be other cell types, eukaryotic or prokaryotic, that express the P protein. Typically, expression of the P protein in non-melanocyte cells is the result of expression in these cells by recombinant technology means as described supra.

The invention also provides a method of identifying agonists, antagonists, and mimetics of P protein function in a fungal cell assay. As previously described herein, a P protein-encoding nucleic acid can be introduced into cells, e.g., fungal cells, which do not normally express a P protein. These cells can then be used in an assay for the identification of agonists, antagonists, and mimetics of P protein function.

With this method, control fungal cells that express a P protein are contacted with selenite and a measurement of the amount of red pigment formation in the control fungal cells is obtained. Red pigment formation in fungal cells exposed to selenite can be conveniently measure spectrophotometrically at 420 nm (Chaudhuri et al., *Genetics* 145:75-83 (1997)). Next, test fungal cells expressing the P protein are contacted with an agent. The agent-contacted test fungal cells are then contacted with selenite, and a measurement of the amount of red pigment formation in the toxin- and agent-contacted test fungal cells is obtained. By comparing the control cell measurement to the test cell measurement, the agent can be identified as a modifier of P protein function when there is a difference between the control cell measurement and the test cell measurement.

In certain embodiments of this aspect of the invention, the fungal cells are *Saccharomyces cerevisiae* or *Schizosaccharomyces pombe*.

One class compounds that can be used to inhibit the function of P protein are P protein-encoding gene antisense nucleic acids. A "P protein-encoding gene antisense nucleic acid" as used herein refers to an oligonucleotide or polynucleotide molecule having a nucleic acid sequence capable of hybridizing to a portion of a P protein-encoding RNA (preferably mRNA) by virtue of some degree of sequence complementarity. The antisense nucleic acid is complementary to either a coding and/or noncoding region of a P protein mRNA such that it inhibits P protein function by reducing the amount of P protein synthesized.

The antisense nucleic acids of the present invention can be oligonucleotides that are double-stranded or single-stranded, RNA or DNA, or a modification or analog thereof, which can be directly administered to a cell, or to the skin of an animal, or which can be produced intracellularly by transcription of heterologous, introduced sequences.

The P protein-encoding gene antisense nucleic acids of the present invention are at least about 6 nucleotides in length and are more preferably oligonucleotides ranging from about 6 to about 50 oligonucleotides. In specific aspects, the oligonucleotide is at least about 10 nucleotides, at least about 15 nucleotides, at least about 100 nucleotides, or at least about 200 nucleotides in length. The oligonucleotides can be DNA or RNA, or chimeric mixtures or derivatives thereof, and modified versions thereof, which can either be single-stranded or double-stranded. The oligonucleotides can be modified at the base moiety, sugar moiety, or phosphate backbone level. The oligonucleotide may include other appending groups such as peptides, or agents facilitating transport across the cell membrane (see, e.g., Letsinger et al., 1989, *Proc. Natl. Acad. Sci.* (*USA*) 86:6553-6556; Lemaitre et al., 1987, *Proc. Natl. Acad. Sci.* (*USA*) 84:648-652; PCT Publication No. WO 88/09810, published Dec. 15, 1988), hybridization-triggered cleavage agents (see, e.g., Krol et al., 1988, *BioTechniques* 6:958-976), or intercalating agents (see, e.g., Zon, 1988, *Pharm. Res.* 5:539-549). In a preferred aspect of the present invention, a P protein-encoding gene antisense oligonucleotide is a single-stranded DNA molecule.

The oligonucleotide may be modified at any position on its structure with substituents generally known in the art. The P protein-encoding gene antisense oligonucleotide may comprise at least one modified base moiety which is selected from a group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5●-methoxycarboxymethyluracil, 5-methoxyuracil, 2-methylthio- N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the antisense oligonucleotide comprises at least one modified sugar moiety selected from a group including, but not limited to, arabinose, 2-fluoroarabinose, xylulose, and hexose. In yet another embodiment, the oligonucleotide comprises at least one modified phosphate backbone component selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof. In yet another embodiment, the oligonucleotide is an alpha-anomeric oligonucleotide. An alpha-anomeric oligonucleotide forms specific double-stranded hybrids with complementary RNA in which, contrary to the usual beta-units, the strands run parallel to each other (Gautier et al., 1987, *Nucl. Acids Res.* 15:6625-6641).

The oligonucleotide may be conjugated to another molecule such as, e.g., a peptide, hybridization triggered cross-linking agent, transport agent, hybridization-triggered cleavage agent, etc.

Oligonucleotides of the present invention may be synthesized by standard methods known in the art including, e.g. by use of an automated DNA synthesizer (such as are commercially available from Biosearch, Applied Biosystems, etc.). As examples, phosphorothioate oligonucleotides may be synthesized by the method of Stein et al., 1988, *Nucl. Acids Res.* 16:3209, and methylphosphonate oligonucleotides can be prepared by use of controlled pore glass polymer supports using the method of Sarin et al., 1988, *Proc. Natl. Acad. Sci.* (*USA*) 85:7448-7451, etc.

In a specific embodiment, the P protein antisense oligonucleotide comprises catalytic RNA, or a ribozyme (see, e.g., PCT International Publication WO 90/11364, published Oct. 4, 1990; Sarver et al., 1990, *Science* 247:1222-1225). In another embodiment, the oligonucleotide is a 2'-0-methylribonucleotide (Inoue et al., 1987, *Nucl. Acids Res.* 15:6131-6148), or a chimeric RNA-DNA analogue (Inoue et al., 1987, *FEBS Lett.* 215:327-330).

In an alternative embodiment, the P protein-encoding gene antisense nucleic acid of the invention is produced intracellularly by transcription from an heterologous sequence. For example, a vector is introduced into a cell in vivo, within which cell the vector or a portion thereof is transcribed, producing an antisense nucleic acid (RNA) of the invention. Such a vector contains a sequence encoding the P protein-encoding gene antisense nucleic acid. Such a vector remains episomal or become chromosomally integrated, as long as it can be transcribed to produce the desired antisense RNA. Such vectors can be constructed by standard recombinant DNA technology methods known in the art S Sambrook et al., *Molecular Cloning: A Laboratory Manual*, 3rd edition Cold Spring Harbor Laboratory Press (2001) (ISBN: 0879695765). Vectors can be plasmids, viral vectors, or others known in the art as useful for replication and expression in mammalian cells. Expression of the sequence encoding the P protein-encoding gene antisense RNA can be regulated by any promoter known in the art to act in such cells. Such promoters can be inducible or constitutive, and can include but are not limited to those listed above.

The antisense nucleic acids of the invention comprise a sequence complementary to at least a portion of an RNA transcript of a P protein-encoding gene, preferably a human P protein-encoding gene. However, absolute complementarity, although preferred, is not required, as long as the antisense nucleic acid has sufficient complementarity to be able to hybridize with the RNA, forming a stable duplex. In the case of double-stranded P protein-encoding gene antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a P protein-encoding gene RNA it may contain and still form a stable duplex (or triplex, as the case may be). One skilled in the art can determine the mismatch tolerance by use of standard procedures to, e.g., determine the melting point of the hybridized complex.

Compounds identified by methods of the invention as modulators, antagonists, agonists, or mimetic s of P protein function can serve as the basis for molecular modeling techniques for the design of chemical analogs that are more effective. Examples of molecular modeling systems are the CHARmm® (Polygen Corporation, Waltham, Mass., now Accelrys. San Diego, Calif.) and QUANTA® (Molecular Simulations Inc., San Diego, Calif., now Accelrys, San Diego, Calif.) programs. CHARMm® performs the energy minimization and molecular dynamics functions. QUANTA® performs the construction, graphic modeling and analysis of molecular structure. QUANTA® allows interactive construction, modification, visualization, and analysis of the behavior of molecules with each other.

For example, once a compound that modifies P protein function is identified, the compound can be used to generate a hypothesis. Such a hypothesis can be generated from any one of the preferred compounds of the present invention using, e.g., the program, Catalyst® (Molecular Simulations Inc., San Diego, Calif., now Accelrys. San Diego, Calif.). Furthermore, Catalyst® can use the hypothesis to search proprietary databases such as, for example, the Cambridge small molecule database (Cambridge, England), as well as other databases or compound libraries, e.g., those cited above, to identify additional examples of the compounds of the present invention.

Compounds identified by methods of the invention as modulators, antagonists, agonists, or mimetics of P protein function can be used to design more effective analogs using modeling packages such as Ludi, Insight II®, C²-Minimizer and Affinity (Molecular Simulations Inc., San Diego, Calif., now Accelrys. San Diego, Calif.). A particularly preferred modeling package is MacroModel® (Columbia University, New York, N.Y.).

Compounds identified by methods of the invention as modulators, antagonists, agonists, or mimetics of P protein function can further be used as the basis for developing a rational combinatorial library that can be screened to identify more effective compounds. While the nature of the combinatorial library is dependent on various factors, such as the particular compound chosen from the preferred compounds of the present invention to form the basis of the library, as well as the desire to synthesize the library using a resin, it will be recognized that the compounds of the present invention provide requisite data suitable for combinatorial design programs such as C²-QSAR (Molecular Simulations Inc., San Diego, Calif., now Accelrys, San Diego, Calif.).

The invention also provides methods of stimulating melanogenesis. Melanocytes can be contacted with agonists of P protein function, identified by way of the methods of the invention based on cell viability/cell death and/or measurement of glutathione content in a cell, in order to stimulate melanogenesis in such cells.

The stimulation of melanogenesis can be determined by obtaining a measurement of a variable known to be important for melanogenesis. For example, the level and/or activity of tyrosinase, an important enzyme for melanin production, can be measured using methods known in the art. Another means of monitoring stimulation of melanogenesis is to determine that there is an increase in melanin, which can be done by simple visual inspection or by measurement of the amount of melanin in cells using techniques known in the art.

Methods of inhibiting melanogenesis are also provided in which antagonists of P protein function, identified by way of the methods of the invention based on cell viability/cell death and/or measurement of glutathione content in a cell, can be used to contact a melanocyte in order to inhibit melanogenesis in such a cell. Inhibition of melanogenesis can be determined by using the same assays used to determine stimulation of melanogenesis.

For methods of stimulating melanogenesis and methods of inhibiting melanogenesis, melanocytes can be contacted in vitro or in vivo using an appropriate pharmaceutical carrier as described herein or known in the art.

The invention also provides pharmaceutical compositions comprising agonists, antagonists, and/or mimetics of P protein function identified by way of the methods of the invention based on cell viability/cell death and/or measurement of glutathione content in a cell.

The pharmaceutical compositions of the invention comprise a pharmaceutically acceptable carrier and an effective amount of a compound that is an antagonist, agonist, and/or a mimetic of P protein function. This composition is administered to a patient, person, or animal having a disease, disorder, or condition that is of a type that results in the underproduction, or overproduction of melanin.

The amount of compound which will be effective in the treatment of a particular disease, disorder, or condition will depend on the nature of the disease, disorder, or condition, and can be determined by standard clinical techniques. Where possible, it is desirable to determine in vitro the cytotoxicity of the compound to the tissue type to be treated, and then in a useful animal model system prior to testing and use in humans.

In addition to pharmaceutical uses, the methods of the current invention are useful for cosmetic purposes. Cosmetic applications for methods of the present invention include the topical application of compositions containing one or more compounds to a subject to enhance or otherwise alter the visual appearance of skin or hair. Occurrences in the skin or hair of noticeable but undesired pigmentation as a result of melanin production, overproduction or underproduction can be treated using the pharmaceutical compositions and therapeutic methods of the present invention.

The compound can be administered for the reduction or increase of melanin synthesis by any means that results in contact of the active agent with its site of action, e.g., a melanocyte, in the body of a mammal. The compounds can be administered by any conventional means available for use in conjunction with pharmaceuticals, either as individual therapeutic agents or in a combination of therapeutic agents. Each can be administered alone, but is preferably administered with a pharmaceutical carrier selected on the basis of the chosen route of administration and standard pharmaceutical practice. The pharmaceutical compositions of the invention can be adapted for oral, parenteral, rectal, and preferably topical, administration, and can be in unit dosage form, in a manner well known to those skilled in the pharmaceutical art. Parenteral administration includes, but is not limited to, injection subcutaneously, intravenously, intraperitoneally or intramuscularly. However, topical application is preferred.

An effective dosage and treatment protocol can be determined by conventional means, starting with a low dose in laboratory animals and then increasing the dosage while monitoring the effects, and systematically varying the dosage regimen as well. Animal studies, preferably mammalian studies, are commonly used to determine the maximal tolerable dose, or MTD, of a bioactive agent per kilogram weight. Those skilled in the art can extrapolate doses for efficacy and avoidance of toxicity to other species, including humans.

Before human studies of efficacy are undertaken, Phase I clinical studies in normal subjects can help establish safe doses. Numerous factors can be taken into consideration by a clinician when determining an optimal dosage for a given subject. Primary among these is the toxicity and half-life of the chosen compound that modifies P protein function. Additional factors include the size of the patient, the age of the patient, the general condition of the patient, the particular disease, condition, or disorder being treated, the severity of the disease, condition, or disorder being treated, the presence of other drugs in the patient, the effect desired, and the like. The trial dosages would be chosen after consideration of the results of animal studies and the clinical literature.

One of ordinary skill in the art will appreciate that the endpoint chosen in a particular case will vary according to the disease, condition, or disorder being treated, the outcome desired by the patient, subject, or treating physician, and other factors. Where the composition is being used to lighten or darken skin color such as, for example, to reverse hyperpigmentation caused by, for example, inflammation or diseases such as melasma, or to lighten or darken hair color, any one of a number of endpoints can be chosen. For example, endpoints can be defined subjectively such as, for example, when the subject is simply "satisfied with the results of the treatment." For pharmacological compositions, the endpoint can be determined by the patients, or the treating physicians, satisfaction with the results of the treatment. Alternatively, endpoints can be defined objectively. For example, the patients or subjects skin or hair in the treated area can be compared to a color chart. Treatment is terminated when the color of the skin or hair in the treated area is similar in appearance to a color on the chart. Alternatively, the reflectance of the treated skin or hair can be measured, and treatment can be terminated when the treated skin or hair attains a specified reflectance. Alternatively, the melanin content of the treated hair or skin can be measured. Treatment can be terminated when the melanin content of the treated hair or skin reaches a specified value. Melanin content can be determined in any way known to the art, including by histological methods, with or without enhancement by stains for melanin.

When the agent or compound that modifies P protein function (i.e., the active ingredient) is administered topically, it can be administered, e.g., as patches, ointments, creams, gels, lotions, solutions, or transdermal administration, described below. The compound can also be administered orally in solid or semi-solid dosage forms, such as hard or soft-gelatin capsules, tablets, or powders, or in liquid dosage forms, such as elixirs, syrups, or suspensions. Additionally, the compound can also be administered parenterally, in sterile liquid dosage forms or in suppository form.

Because in vivo use is contemplated, the composition is preferably of high purity and substantially free of potentially harmful contaminants, e.g., at least National Food (NF) grade, generally at least analytical grade, and preferably at least pharmaceutical grade. To the extent that a given compound must be synthesized prior to use, such synthesis or subsequent purification shall preferably result in a product that is substantially free of any potentially contaminating toxic agents that may have been used during the synthesis or purification procedures.

Useful pharmaceutical dosage forms for administration of compounds that modify P protein function are described below.

The pharmaceutical compositions can be applied directly to the skin. Alternatively, they can be delivered by various transdermal drug delivery systems, such as transdermal patches as known in the art. For example, for topical administration, the active ingredient can be formulated in a solution, gel, lotion, ointment, cream, suspension, paste, liniment, powder, tincture, aerosol, patch, or the like in a pharmaceutically or cosmetically acceptable form by methods well known in the art. The composition can be any of a variety of forms common in the pharmaceutical or cosmetic arts for topical application to animals or humans, including solutions, lotions, sprays, creams, ointments, salves, gels, etc., as described below. Preferred agents are those that are viscous enough to remain on the treated area, those that do not readily evaporate, and/or those that are easily removed by rinsing with water, optionally with the aid of soaps, cleansers and/or shampoos.

A topically applied composition of the invention contains a pharmaceutically effective agent that modifies P protein function as described herein, and those ingredients as are necessary for use as a carrier, such as an emulsion, a cream, an ointment, an ophthalmic ointment, an aqueous solution, a lotion or an aerosol. Non-limiting examples of such carriers are described in more detail below and may be found in International Patent Publication WO 00/62742, published Oct. 26, 2000, U.S. Pat. No. 5,691,380 to Mason et al., issued on Nov. 25, 1997; and U.S. Pat. No. 5, 968,528 to Deckner et al., issued on Oct. 19, 1999; U.S. Pat. No. 4,139,619 to Chidsey, III, issued on Feb. 13, 1979; and U.S. Pat. No. 4,684,635 to Orentreich et al., issued on Aug. 4, 1987 which are incorporated herein by reference. Suitable pharmaceutical carriers are further described in *Remington's Pharmaceutical Sciences,* 17th ed., Mack Publishing Company, Easton, Pa. (1990) a standard reference text in this field.

Actual methods for preparing topical formulations are known or apparent to those skilled in the art, and are described in detail in *Remington's Pharmaceutical Sciences,* 1990 (supra); and *Pharmaceutical Dosage Forms and Drug Delivery Systems,* 6th ed., Williams & Wilkins (1995). Other sources of information include, but are not limited to, the *CTFA Cosmetic Ingredient Handbook,* Second Edition (1992), Sagarin, *Cosmetics, Science and Technology,* 2nd Edition, Vol. 1, pp. 3243 (1972) and/or *McCutcheon's. Detergents and Emulsifiers,* North American Edition (1986), published by Allured Publishing Corporation.

In another aspect, the invention provides a method of treating a patient having cancer. The method comprises contacting cancer cells with an agonist or mimetic of P protein function, the agonist or mimetic of P protein function identified by way of the methods of the invention based on cell viability/cell death and/or measurement of glutathione content in a cell. Once the cells are sensitized by the preceding treatment, the cancer cells are then contacted with a chemotherapeutic agent. In one embodiment, the cancer treated is selected from the group consisting of liver cancer, pancreatic cancer, lung cancer, colon cancer, intestinal cancer, stomach cancer, brain cancer, a leukocytic cancer, bone cancer, ovarian cancer, testicular cancer, and melanoma cancer.

Pharmaceutical compositions of the invention do not include modifiers of P protein function such as imipramine and other tricyclic amines such as amitriptyline, trimipramine, or doxepin, or those compounds that lack structural similarity with imipramine, but share the functional property with imipramine of being useful antidepressants, such as the atypical antidepressants (e.g., trazodone and fluoxetine. In addition, bafilomycin A1 and concanamycin A are excluded from the pharmaceutical compositions of the invention, since these compounds are known to modify P protein function (see, e.g., published U.S. Ser. No. 09/827,428).

Melanomas are any group of malignant neoplasms primarily of the skin that are composed of melanocytes. Most melanomas develop from a pigmented benign congenital skin blemish termed a nevus over a period of several months or years and occur most frequently in fair skinned people having light colored eyes. Melanomas occur as black or brown spots having an irregular border, pigment appearing to radiate beyond the border width and/or a red, black, or blue coloration observable on close examination. Sometimes a nodular surface is suggestive of a melanoma. Different types of melanomas include, but are not limited to: amelanotic, benign juvenile, lentigo maligna, primary cutaneous, and superficial spreading.

The administration of the P protein agonist and/or P protein mimetic and chemotherapeutic agent can take place by any suitable technique, including parenteral administration. Examples of parenteral administration include intravenous, intraarterial, intramuscular, subcutaneous, and intraperitoneal, with intravenous, intramuscular, and subcutaneous administration. Moreover, the application of the P protein agonist or the chemotherapeutic agent can be separately administered in any order or administered together.

The dose and dosage regimen will depend mainly on the degree of malignancy, the chemotherapeutic agent, the agonist and/or mimetic of P protein function being utilized, the patient, the patient's history, and the patient's response to treatment. The amount must be effective to result in clinical improvement. The doses of either compound may be single doses or multiple doses. If multiple doses are employed, the frequency of administration (schedule) will depend, for example, on the patient, type of tumor response, dosage amounts the chemotherapeutic agent and agonist of P protein function, etc. Administration once a week may be effective, whereas for others, daily administration or administration every other day or every third day may be effective. The practitioner will be able to ascertain upon routine experimentation, which route of administration and frequency of administration are most effective in any particular case.

The dosage amount for the chemotherapeutic agent and the agonist and/or mimetic of P protein function that appears to be most effective herein is one that results in remission, no appearance, or decreased tumor burden and is not toxic or is acceptably toxic to the patient, as defined by the protocol in Example 1 below. Generally, such conditions as fever, chills, and general malaise are considered acceptable. This optimum dose level will depend on many factors, for example, on the type of patient, the response of the patient, the type of tumor, route and schedule of administration, existing tumor burden, and the definition of toxicity. For example, toxicity to the human patient may be defined by the extent and type of side effects, with fever, chills, and general malaise considered acceptable toxicity for purposes herein.

As will be obvious to those skilled in the art, the invention having established that P protein-expressing cells are more sensitive to toxins also provides in another aspect a method of increasing the sensitivity of a cell that does not express a P protein to a toxin. The method comprises (a) introducing into the cell a nucleic acid molecule encoding the P protein that enables the expression of the P protein in the cell; and (b) expressing the P protein in the cell at a sufficient level to increase sensitivity of the cell to the toxin.

In another aspect, the invention provides a method of increasing the sensitivity to a toxin of a cell that does not express a P protein. The method comprises contacting the cell with a P protein mimetic.

Cells useful in this aspect of the invention include mammalian cells, e.g., human, rat, mouse, hamster, or guinea pig, avian cells, fish cells, nematode cells, insect cells, plant cells, fungal cells, or bacterial cells.

As will be understood by those in the art, the compositions and pharmaceutical compositions of the invention may be provided in the form of a kit. Kits of the invention comprise one or more specific compositions and/or pharmaceutical compositions of the invention that modify P protein function, in a container. Optionally, the kit further contains printed instructions as a label or package insert directing the use of such reagents to modulate skin pigmentation, i.e., to either lighten or darken skin as appropriate to the particular included composition. These compounds are provided in a container designed to prevent contamination, minimize evaporation or drying of the composition, etc. The compounds may or may not be provided in a preset unit dose or usage amount. In a similar fashion, the invention also provides kit comprising therapeutic treatments as described herein for melanoma.

The following examples illustrate the preferred modes of making and practicing the present invention but are not meant to limit the scope of the invention since alternative methods may be utilized to obtain similar results.

EXAMPLES

Example 1

Toxicity Screening In Melanocytes

The differential affect of various toxins on melanocytes expressing and not expressing the P protein was determined by examining the survival rates of wild-type melan-a melanocytes (A) and P-null melanocytes (P) after exposure to various toxins.

The assays were set up by first trypsinizing cell cultures and resuspending the cells to a final concentration of $1.5 \times 10^5$ cells/milliliter in RPMI 1640 media (Gibco-BRL, Rockville, Md.). 96-well dishes were plated by adding 100 µl of the cell suspension per well. Cells were allowed to attach overnight at 37° C. Cell plating was adjusted as necessary to that the cultures would be approximately 80% confluent after an overnight culture.

After 24 hours, the media was removed and replaced with the appropriate concentration of compound in 100 µl of complete media. Following a 72-hour incubation, a cell viability assay was performed using the Promega CellTiter 96 proliferation assay (Promega Corporation, Madison, Wis.). The kit allows for colorimetric quantitation of viable cells using bioreduction of a tetrazolium compound. The growth or death rate was expressed as $OD_{490}$ of cells in treated well/$OD_{490}$ of cells in untreated well.

Wild-type cells (i.e., P protein-expressing cells) were found to be more sensitive to many toxins than p-null cells. The results are summarized in Table 1.

TABLE 1

CHANGES IN TOXIN SENSITIVITY AS A FUNCTION OF P PROTEIN EXPRESSION

| | TOXIN SENSITIVITY INCREASE | TOXIN SENSITIVITY DECREASE | TOXIN SENSITIVITY NO CHANGE |
|---|---|---|---|
| ARSENATE | ✓ | | |
| ARSENIC TRIOXIDE | ✓ | | |
| ANTIMONY | ✓ | | |
| IRON SULFATE (FESO₄) | ✓ | | |
| VINBLASTINE | ✓ | | |
| FCCP | ✓ | | |
| PRIMAQUINE | | | ✓ |
| CYCLOHEXIMIDE | ✓ | | |
| BAFILOMYCIN Al | ✓ | | |
| ARSENITE | ✓ | | |
| ETHACRYNIC ACID | ✓ | | |
| CADMIUM | ✓ | | |
| CISPLATIN | ✓ | | |
| BUTHIONINE SULFOXIMINE (BSO) | ✓ | | |
| SELENATE | ✓ | | |
| DOXORUBICIN | ✓ | | |
| ALLYLGLYCINE | | | ✓ |
| OLIGOMYCIN | ✓ | | |
| SELENATE | ✓ | | |
| VERAPAMIL | ✓ | | |
| CHLOROQUINE | | ✓ | |

TABLE 1-continued

CHANGES IN TOXIN SENSITIVITY AS A FUNCTION
OF P PROTEIN EXPRESSION

| | TOXIN SENSITIVITY INCREASE | TOXIN SENSITIVITY DECREASE | TOXIN SENSITIVITY NO CHANGE |
|---|---|---|---|
| AMPHOTERICIN | | | ✓ |
| VALINOMYCIN | | ✓ | |
| LITHIUM | | | ✓ |

Example 2

Glutathione Content in Wild-Type and P-Null Melanocytes

Experiments were conducted in order to determine the affect of P protein expression on the intracellular level of glutathione (GSH). GSH content was measured using the GT-20 colorimetric assay kit (Oxford Biomedical Research, Inc., Oxford, Mich.). The assay is a kinetic enzymatic recycling assay based on the oxidation of GSH by 5,5'-dithiobis-(2-nitrobenzoic acid) [DTNB] to measure the total glutathione (tGSH) content of biological samples. Glutathione standards or treated samples are added to the microtiter plate wells, followed by DTNB and glutathione reductase. The addition of NADPH2 to the wells initiates the progressive reduction of DTNB by GSH, causing a color increase that is monitored spectrophotometrically at 405 nm. The rate of color change, typically followed over a 4 minute time period, is proportional to the tGSH concentration.

Consequently, the concentration of tGSH in unknown samples may be determined by reference to a standard curve produced following directions provided in the kit. GSH reacts with DTNB to produce a colored ion, which absorbs light at 405 nm, and a mixed disulphide. This disulphide reacts with further quantities of GSH present to liberate another ion and GSSG. GSSG is reduced enzymatically to GSH which then re-enters the cycle. Since GSSG represents only a small percentage of total acid-solution free glutathione, the resulting values for tGSH (which encompasses both GSH and GSSG) are expressed in units of GSH equivalents.

Glutathione content was determined in wild-type melan-a (A) and P-null melan-p1 (P) cells. Cells grown to confluence were harvested by trypsinization, washed twice with phosphate buffered saline and resuspended in 2 ml of 5% metaphosphoric acid (MPA). 100 µl was removed and the protein concentration determined (Biorad, Richmond, Calif.). The volume was adjusted such that each suspension contained an equal concentration of protein. The supernatant was assayed to determine the amount of glutathione present.

Figure 2:
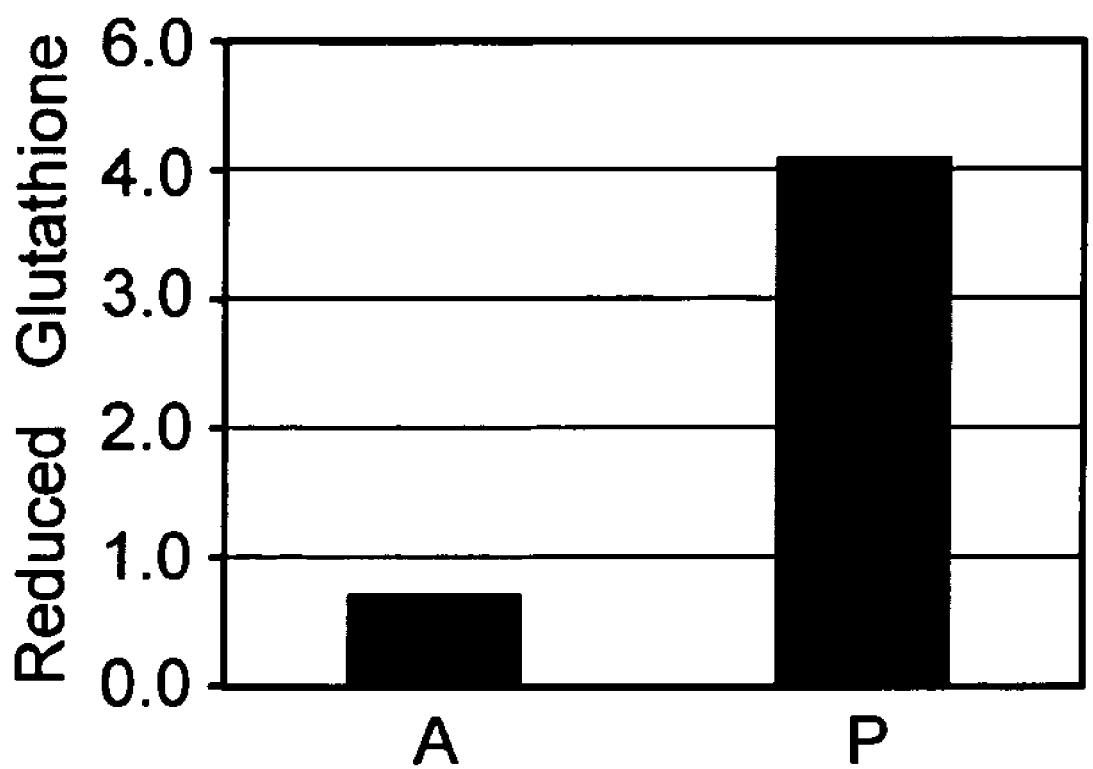

Melanocytes expressing P protein (A) were found to have 3-fold less glutathione than P-null cells (P) (FIG. 2). The lower amount of glutathione in P protein expressing melanocytes is consistent with the increased sensitivity of these cells to toxins, given the role of glutathione in toxin clearance from cells.

Example 3

Toxicity Screening in Yeast

Yeast cells were examined as a model system for screening for compounds that modify P protein function. As a first step, the sensitivity of yeast cells that express the P protein to toxins was examined.

In order to introduce P protein expression into yeast cells, the open reading frame of the mouse P gene encoding cDNA was amplified by polymerase chain reaction using oligonucleotides that corresponded to the 5' (5'-ATCGA GGATCATGCGCCTAGAGAACAAAG-3', BamHI underlined) and 3' (SEQ ID NO:1) (5'-CTCTA GATATCTTAATGGTGATGGTGAGATGATTCCATC CACCACAAT-3' (SEQ ID NO:2), EcoRV site underlined, HIS6 tag shown in italic). The PCR product was cut with BamHI and EcoRV and subcloned into centromeric expression vectors p413GPD (American Type Culture Collection (ATTC), Manassas, Va.), which has a his3 marker to generate p413GPD-P. The plasmid p413GPDpdel was used as a control in the experiments. It was obtained after restriction digestion of the plasmid p413GPDp with HindIII, resulting in the removal of the region between 625 and 1717 nucleotides of the mouse P protein encoding cDNA.

Strain SH3866 (leu2 ura3 his4 ade6 pep4gal2 (obtained from Dr. Satoshi Hiroshima, Department of Biotechnology, Osaka University, Japan)) was transformed with centromeric plasmid p416GPDp and control plasmid p413GPD. A quantitative drug assay was performed using a method similar to that of Egner et al. (*Mol. Bio. Cell.* 9:523-543 (1998)).

The sensitivity of P protein-expressing yeast cells to arsenate, arsenic trioxide, and antimony was examined by determining the extent of colony growth on media containing various concentrations of these compounds. Actively growing yeast cultures were plated at a concentration of $1 \times 10^{-3}$ cells per well, and the plates were incubated at 30° C. for 3 days.

Figure 3A:
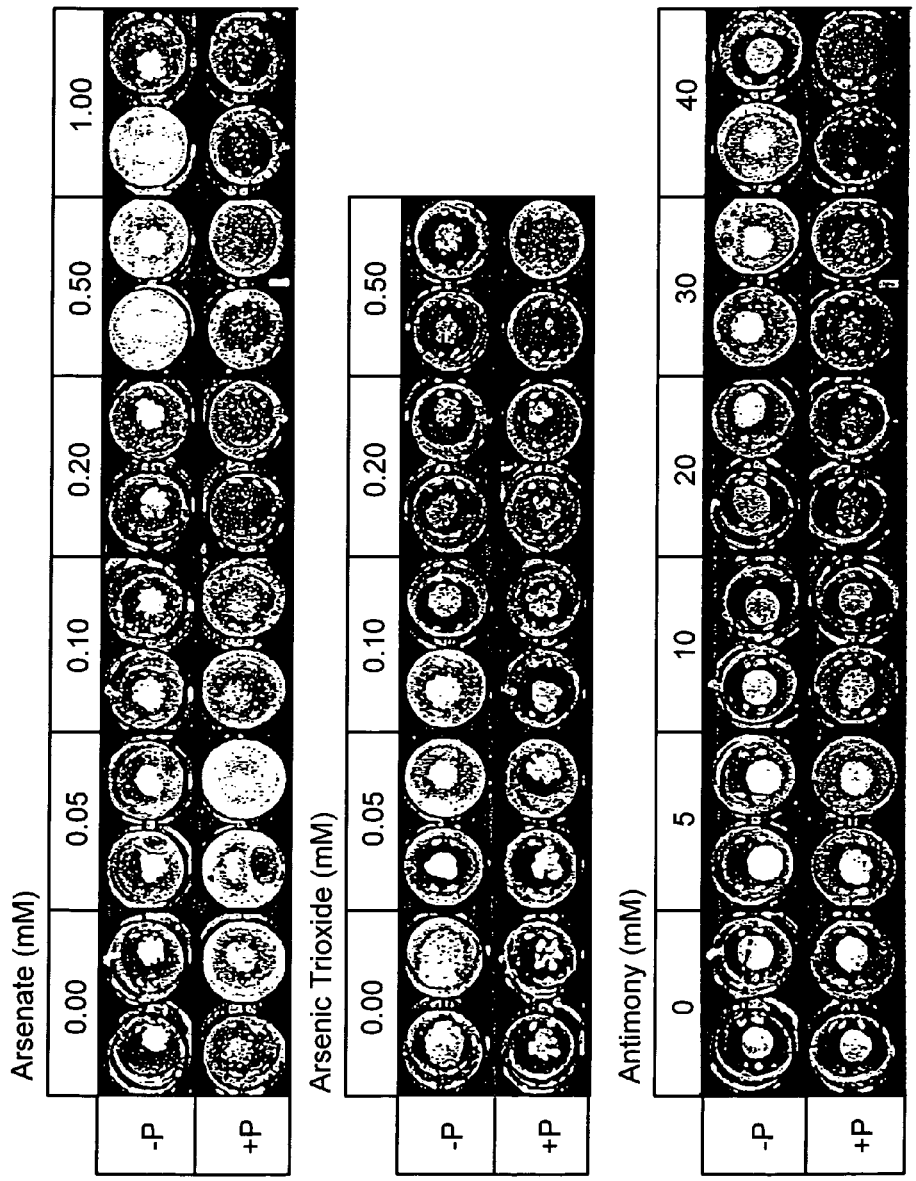

Results presented in FIG. 3A demonstrate that yeast cell colonies expressing a P protein and exposed to arsenate, arsenic trioxide, and antimony do not reach the same size as colonies exposed to the same compounds that do not express the P protein. For the experiments whose results are shown in FIG. 3A, twenty-four well plates were prepared using selective medium-agar. The indicated concentrations of drug were added prior to pouring. Actively growing cultures were plated at a concentration of $1 \times 10^{-3}$ per well. Ten microliters of the diluted culture was then spotted onto each well, and the plates were incubated at 30° C. for 3 days.

In another experiment, P protein-expressing yeast cells and control yeast cells were exposed to various concentrations of selenite. The toxic affect of selenite in yeast is believed to be due to DNA damage. The major mode of selenite detoxification appears to be its reduction by glutathione to elementary selenium that accumulates as a red precipitate in the cell vacuole (Pinson et al. *Molecular Microbiology* 36:679-687(2000)).

10 mM, 20 mM, 30 mM, 40 mM, and 50 mM selenite solutions were prepared in 55° C. selective medium-agar and plated in duplicate into 24-well plates. Actively growing yeast cultures were diluted to A600 values of 0.001, and then 10 µl aliquots were spotted in duplicate onto the selenite-containing agar medium. Plates were incubated at 30° C. for 3 days.

Figure 3B:
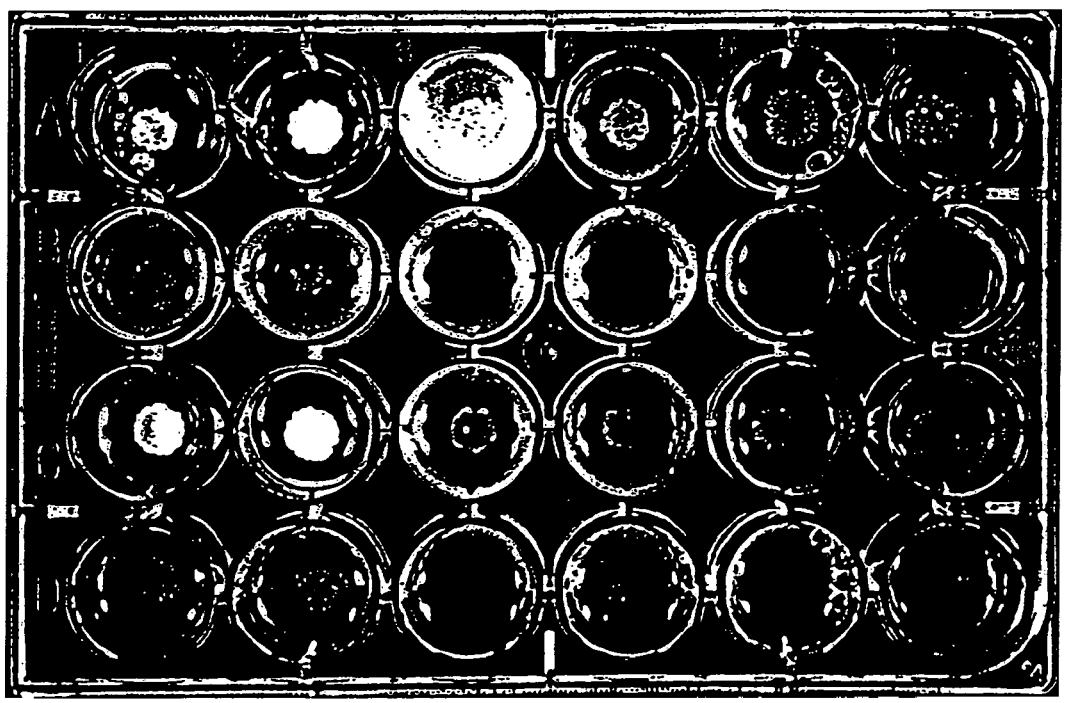

Referring to FIG. 3B, wells A1 and A2 represent the control cells not treated with selenite; wells A3 and A4 represent the control cells treated with 10 mM selenite; wells A5 and A6 represent the control cells treated with 20 mM selenite; wells B1 and B2 represent the control cells treated with 30 mM selenite; wells B3 and B4 represent the control cells treated with 40 mM selenite; wells B5 and B6 represent the control cells treated with 50 mM selenite, wells C1 and C2 represent P-expressing cells not treated with selenite, wells C3 and C4 represent the control cells treated with 10 mM selenite, wells C5 and C6 represent the control cells treated with 20 mM selenite, wells D1 and D2 represent the control cells treated with 30 mM selenite, wells D3 and D4 represent the control cells treated with 40 mM selenite, and wells D5 and D6 represent the control cells treated with 50 mM selenite.

These experiments show that P-expressing cells accumulate more red precipitate than the control cells, indicating that these cells have converted more selenite to selenium. P protein antagonists should block the accumulation of red pigment in P protein-expressing yeast treated with selenite.

Also, the results presented in FIG. 3B demonstrate that there is no difference in selenite sensitivity for cells expressing a P protein versus control cells (i.e., no P protein expression).

Similar experiments were conducted to examine the affect of nigericin on cell viability. The results of these experiments indicated that yeast cells expressing the P protein had an $IC_{50}$ value of 3 µM for nigericin, while yeast cells not expressing the P protein had an $IC_{50}$ value of 25 µM for nigericin (data not shown).

Example 4

Glutathione Content in P Protein-Expressing Yeast

Cellular glutathione content was measured by glutathione colorimetric assay as described in Example 2 for P protein-expressing cells and control. The assay was performed in yeast strain SH3866 leu2 ura3 his4 ade6 pep4gal2, source Satoshi Harashima, Department of Biotechnology, Osaka University, Japan, and glutathione was estimated by the 5,5' dithiobis-(2 nitrobenzoic acid) (DTNB)-glutathione reductase coupled reaction. Cells were harvested, washed twice with water, resuspended in 0.4 ml of 5% sulphosalicylic acid, mixed with an equal volume of glass beads, and broken by vigorous bead beating at 4° C. for a total of 6 min. The extracts were spun down in a microfuge to remove the glass beads and also the cell debris and protein precipitate. The supernatant was assayed to determine the amount of glutathione.

As presented in Table 2, results of the experiment indicate that the expression of P protein leads to 10-fold depletion of glutathione in the yeast cells, providing some explanation of the increased sensitivity of these cells to toxins given the role of glutathione in toxin clearance from cells.

TABLE 2

MEASUREMENT OF GLUTATHIONE IN YEAST CELLS EXPRESSING AND NOT EXPRESSING P PROTEIN

| Yeast Cells | GSH Content (nM/$10^7$ cells) |
|---|---|
| Transformed With Control Plasmid p416GPD | 3.9 |
| Transformed With Plasmid p p413GPD-P (Expresses p protein) | 0.35 |

EQUIVALENTS

Those skilled in the art will recognize, or be able to ascertain, using no more than routine experimentation, many equivalents to the specific embodiments of the invention described herein. Such equivalents are intended to be encompassed by the following claims.

What is claimed is:

1. A method of identifying an agent that modifies the viability of a cell expressing p (pink eyed dilution) protein, the method comprising:
   (a) contacting control cells expressing a p protein with a toxin and obtaining a measurement of the viability or death of the control cells contacted with the toxin;
   (b) contacting test cells expressing the p protein with a candidate agent;
   (c) contacting the agent-contacted test cells with the toxin and obtaining a measurement of the viability or death of the agent-contacted test cells contacted with the toxin, the toxin being different than the agent;
   (d) comparing the control cell measurement of step (a) to the test cell measurement of step (c); and
   (e) identifying the agent as a modifier of the viability of a cell expressing p protein, if the test cells, which were contacted with the agent and toxin, are more or less sensitive to the toxin than the control cells, which were not contacted with the agent, when there is a difference between the control cell measurement and the test cell measurement.

2. The method of claim 1, wherein the toxin is selected from the group consisting of:
   (a) a metalloid,
   (b) a metal,
   (c) a glutathione depleting agent,
   (d) a chemotherapeutic agent,
   (e) an ionophore,
   (f) a vacuolar-type ATPase inhibitor,
   (g) a microtubule inhibitor, and
   (h) a DNA interacting agent.

3. The method of claim 2, wherein the toxin is a metalloid selected from the group consisting of arsenate, arsenic trioxide, and antimony.

4. The method of claim 2, wherein the toxin is the metal ferrous sulfate.

5. The method of claim 2, wherein the toxin is a glutathione depleting agent selected from the group consisting of ethacrynic acid and buthionine sulfoximine.

6. The method of claim 1, wherein the toxin is a chemotherapeutic agent selected from the group consisting of doxirubicin and vinblastin.

7. The method of claim 2, wherein the toxin is the ionophore monensin.

8. The method of claim 2, wherein the toxin is the vacuolar-type ATPase inhibitor bafilomycin A.

9. The method of claim 2, wherein the toxin is a DNA interacting agent selected from the group consisting of doxirubicin and cisplatin.

10. The method of claim 1, wherein the test cells are selected from the group consisting of mammalian cells, plant cells, and fungal cells.

11. The method of claim 10, wherein the test cells are mammalian cells.

12. The method of claim 11, wherein the mammalian cells are melanocytes.

13. The method of claim 10, wherein the test cells are plant cells.

14. The method of claim 10, wherein the test cells are fungal cells.

15. The method of claim 1, wherein the p protein is a recombinant p protein.

16. The method of claim 1, wherein the p protein is a mammalian p protein.

17. The method of claim 16, wherein the p protein is a human p protein.

18. The method of claim 16, wherein the p protein is a mouse p protein.

19. A method of identifying an agent that modifies the viability of a cell expressing p protein, the method comprising:
   (a) obtaining a measurement of the amount of glutathione in control cells expressing a p protein;
   (b) contacting test cells expressing the p protein with an agent;
   (c) obtaining a measurement of the amount of glutathione in test cells contacted by the agent;
   (d) comparing the control cell measurement to the test cell measurement; and
   (e) identifying the agent as a modifier of a cell expressing p protein when there is a difference between the control cell measurement and the test cell measurement.

20. The method of claim 19, wherein the test cells are selected from the group consisting of: mammalian cells, plant cells, and fungal cells.

21. The method of claim 20, wherein the test cells are mammalian cells.

22. The method of claim 21, wherein the mammalian cells are melanocytes.

23. The method of claim 20, wherein the test cells are plant cells.

24. The method of claim 20, wherein the test cells are fungal cells.

25. The method of claim 19, wherein the p protein is a recombinant p protein.

26. The method of claim 19, wherein the p protein is a mammalian p protein.

27. The method of claim 26, wherein the p protein is a human p protein.

28. The method of claim 26, wherein the p protein is a mouse p protein.

* * * * *